United States Patent
Lee et al.

(10) Patent No.: US 9,434,610 B2
(45) Date of Patent: *Sep. 6, 2016

(54) HPMA—DOCETAXEL CONJUGATES AND USES THEREFORE

(75) Inventors: Young B. Lee, Clarksburg, MD (US); Deog J. Kim, Rockville, MD (US); Chang H. Ahn, Potomac, MD (US); Anjan Nan, Hanover, MD (US); Hamidreza Ghandehari, Salt Lake City, UT (US); Abhijit Ray, Salt Lake City, UT (US)

(73) Assignees: REXAHN PHARMACEUTICALS, INC., Rockville, MD (US); University of Maryland, Baltimore, Baltimore, MD (US)

( * ) Notice: Subject to any disclaimer, the term of this patent is extended or adjusted under 35 U.S.C. 154(b) by 1000 days.

This patent is subject to a terminal disclaimer.

(21) Appl. No.: 12/575,276

(22) Filed: Oct. 7, 2009

(65) Prior Publication Data
US 2010/0099644 A1  Apr. 22, 2010

Related U.S. Application Data

(60) Provisional application No. 61/103,390, filed on Oct. 7, 2008.

(51) Int. Cl.
A61K 47/48 (2006.01)
A61P 35/00 (2006.01)
B82Y 5/00 (2011.01)

(52) U.S. Cl.
CPC ............ B82Y 5/00 (2013.01); *A61K 47/48107* (2013.01); *A61K 47/48176* (2013.01); *A61K 47/48246* (2013.01); *A61K 47/48338* (2013.01)

(58) Field of Classification Search
CPC ............ B82Y 5/00; A61K 47/48107; A61K 47/48176; A61K 47/48246; A61K 47/48338
See application file for complete search history.

(56) References Cited

U.S. PATENT DOCUMENTS

| | | | |
|---|---|---|---|
| 3,931,111 A | 1/1976 | Kopecek et al. | |
| 3,931,123 A | 1/1976 | Vacik et al. | |
| 3,997,660 A | 12/1976 | Kopecek et al. | |
| 4,062,831 A | 12/1977 | Kopecek et al. | |
| 4,074,039 A | 2/1978 | Lim et al. | |
| 4,097,470 A | 6/1978 | Drobnik et al. | |
| 5,037,883 A | 8/1991 | Kopecek et al. | |
| 5,258,453 A | 11/1993 | Kopecek et al. | |
| 5,965,118 A * | 10/1999 | Duncan et al. | 424/78.27 |
| 6,342,221 B1 | 1/2002 | Thorpe et al. | |
| 6,346,349 B1 | 2/2002 | Briscoe et al. | |
| 6,348,209 B2 | 2/2002 | Placke et al. | |
| 6,692,734 B2 * | 2/2004 | Stewart et al. | 424/78.27 |
| 7,166,733 B2 | 1/2007 | Nowotnik et al. | |
| 8,846,110 B2 * | 9/2014 | Lee | A61K 31/337 424/649 |
| 2001/0038830 A1 | 11/2001 | Stewart et al. | |
| 2001/0041189 A1 * | 11/2001 | Xu | 424/488 |
| 2002/0077279 A1 | 6/2002 | Kumar et al. | |
| 2002/0103259 A1 | 8/2002 | Martinez et al. | |
| 2004/0234497 A1 | 11/2004 | Luo et al. | |
| 2005/0013818 A1 * | 1/2005 | Karin et al. | 424/155.1 |
| 2005/0129769 A1 | 6/2005 | Barry et al. | |
| 2005/0196343 A1 | 9/2005 | Reddy et al. | |
| 2005/0287114 A1 | 12/2005 | Wang et al. | |
| 2006/0014695 A1 | 1/2006 | Ghandehari et al. | |
| 2006/0269479 A1 | 11/2006 | Colton et al. | |
| 2007/0287680 A1 | 12/2007 | Cuchelkar et al. | |
| 2008/0193377 A1 | 8/2008 | Line et al. | |
| 2009/0104143 A1 | 4/2009 | Luo et al. | |

FOREIGN PATENT DOCUMENTS

| | | |
|---|---|---|
| FR | 2 858 936 A1 | 2/2005 |
| JP | S61-243026 A | 10/1986 |
| JP | 2003-511423 A | 3/2003 |
| JP | 2005-535604 A | 11/2005 |
| JP | 2008-515915 A | 5/2008 |
| WO | WO-0066091 A1 | 11/2000 |
| WO | WO-02/07770 A2 | 1/2002 |
| WO | WO-03/1014250 A2 | 12/2003 |
| WO | WO-2006/042146 A2 | 4/2006 |
| WO | WO-2006113666 A2 | 10/2006 |
| WO | WO-2007067417 A1 | 6/2007 |
| WO | WO-2008/034391 A1 | 3/2008 |
| WO | WO-2008/076771 A2 | 6/2008 |

OTHER PUBLICATIONS

Int J Pharm. Jan. 13, 2006;307(2):258-69. Epub Nov. 17, 2005. Folate-mediated targeting of polymeric conjugates of gemcitabine. Cavallaro G, Mariano L, Salmaso S, Caliceti P, Gaetano G.*
Sampath et al J neurooncol Oct. 2006.*
Lokich et al. Cancer Invest 2003.*
Sigma Aldrich Amino acids Reference Chart, web page on Jul. 8, 2013.*
Mitra, A. et al., "Polymeric conjugates of mono- and bi-cyclic alphaVbeta3 binding peptides from tumor targeting", Journal of controlled Release, Elsevier, Amsterdam, NL, vol. 114, No. 2, Aug. 28, 2006, pp. 175-183.
Putnam et al., Advances in Polymer Science, vol. 122 (Biopolymers II), pp. 55-123, 1995.
Duncan et al., Human and Experimental Toxicology, vol. 17, pp. 93-104, 1998.

(Continued)

*Primary Examiner* — Julie Ha
*Assistant Examiner* — Li Ni Komatsu
(74) *Attorney, Agent, or Firm* — Venable LLP; Keith G. Haddaway; Annette K. Kwok

(57) ABSTRACT

Disclosed are water-soluble compositions of gemcitabine and docetaxel formed by conjugating the gemcitabine or docetaxel to a water-soluble polymer such as N-2-hydroxypropyl methacrylamide (HPMA). Also disclosed are methods of using the compositions of the invention for the treatment of cancer.

19 Claims, 3 Drawing Sheets

(56) References Cited

OTHER PUBLICATIONS

Felding-Habermann et al., Clinical and Experimental Metastasis, vol. 19, pp. 427-436, 2002.
Koivunen et al., Biotechnology, vol. 13, pp. 265-270, 1995.
Arap et al., Science, vol. 279, pp. 377-380, 1998.
Capello et al., Journal of Nuclear Medicine, vol. 45, pp. 1716-1720, 2004.
Kopecek et al., European Polymer Journal, vol. 9, pp. 7-14, 1973.
Kopecek et al., Annals of the New York Academy of Science, vol. 446, pp. 93-104, 1985.
Skehan et al., Journal of the National Cancer Institute, vol. 82, pp. 1107-1112, 1990.
Mitra et al., Journal of Controlled Release, vol. 102, pp. 191-201, 2005.
Borgman et al., Journal of Controlled Release, vol. 132, pp. 193-199, 2008.
Lu et al., Advanced Drug Delivery Reviews, vol. 54, pp. 675-693, 2002.
Choi et al., Journal of Bioactive and Compatible Polymers, vol. 14, pp. 447-456, 1999.
Christie et al., Advanced Drug Delivery Reviews, vol. 55, pp. 421-437, 2003.
U.S. Appl. No. 60/732,633, part of International Application No. PCT/US2006/014483, published as WO 2006/113666 on Oct. 26, 2006.
Duncan et al., Biochimica et Biophysica Acta, vol. 880, pp. 62-71, 1986.
Cavallaro, G. et al., "Folate-mediated targeting of polymeric conjugates of gemcitabine", International Journal of Pharmaceutics, Elsevier BV, NL, vol. 307, No. 2, Jan. 13, 2006, pp. 258-269.
Etrych, T. et al., "Synthesis of HPMA Copolymers Containing Doxorubicin Bound via a Hydrazone Linkage. Effect of Spacer on Drug Release and in vitro Cytotoxicity", Macromolecular Bioscience, Viley Vch Verlag, Veinheim, DE, vol. 2, No. 1, Jan. 1, 2002, pp. 43-52.
International Search Report and Written Opinion for International Application No. PCT/US2009/059869, Dated Apr. 7, 2010.
Kopecek, J. et al., "HPMA copolymer-anticancer drug conjugates: design, activity, and mechanism of action", European Journal of Pharmaceutics and Biopharmaceutics, Elsevier Science Publishers B.V., Amsterdam, NL, vol. 50, No. 1, Jul. 3, 2000, pp. 61-81.
Lammers, T. et al., "Image-guided and passively tumour-targeted polymeric nanomedicines for radiochemotherapy", British Journal of Cancer, vol. 99, Sep. 2, 2008, pp. 900-910.
Pasut, G. et al., "Antitumoral activity of PEG-gemcitabine prodrugs targeted by folic acid", Journal of Controlled Release, Elsevier, Amsterdam, NL, vol. 127, No. 3, May 8, 2008, pp. 239-248.
Putnam, D. et al., "Polymer Conjugates with Anticancer Activity", Advances in Polymer Science, vol. 122, pp. 56-123.
International Search Report and Written Opinion for International Application No. PCT/US2010/052510, dated Jun. 23, 2011.
International Preliminary Report on Patentability issued in International Application No. PCT/US2009/059869 dated Apr. 12, 2011.
International Preliminary Report on Patentability issued in International Application No. PCT/US2010/052510 dated Apr. 17, 2012.
Office Action issued in European Application No. 09793342.8 dated Oct. 9, 2012.
Office Action issued in Chinese Application No. 200980148874.9 dated Aug. 23, 2012.
Drug Bank, "Docetaxel," Accessed: Dec. 19, 2002, pp. 1-8, URL: http://www.drugbank.ca/drugs/DB01248.
IPCS Inchem, "Cisplatin," Accessed Dec. 19, 2012, pp. 1-43, URL: http://www.inchem.org/documents/pims/pharm/cisplat.htm.
Lammers et al., "Simultaneous delivery of doxorubicin and gemcitabine to tumors in vivo using prototypic polymeric drug carriers," Biomaterials 30: 3466-3475 (2009)).
Statement of relevance of Mexican Office Action issued in Mexican Patent Application No. MX/a/2011/003738.
Office Action issued in Australian Patent Application No. 2009302387 dated Jan. 20, 2014.
Office Action issued in Chinese Patent Application No. 200980148874.9 dated Aug. 29, 2013.
Office Action issued in Chinese Patent Application No. 201080055030.2 dated Apr. 26, 2013.
Office Action issued in Chinese Patent Application No. 201080055030.2 dated Mar. 7, 2014.
Office Action issued in Japanese Patent Application No. 2011-531149 dated Oct. 1, 2013.
Office Action issued in U.S. Appl. No. 12/903,927 dated Nov. 29, 2013.
Park et al., "Biodegradable Polymers for Microencapsulation of Drugs," Molecules 2005, 10, 146-161.
Andoulakis et al., "Treatment of Pancreatic Cancer with Docetaxel and Granulocyte Colony-Stimulating Factor: A Multicenter Phase II Study", J. Clin. Oncol., 17(6) (Jun. 1999) 1779-1785.
Bedikian et al., "Phase II Trial of Docetaxel in Patients With Advanced Cutaneous Malignant Melanoma Previously Untreated With Chemotherapy", J. Clin. Oncol., 13(12) (Dec. 1995) 2895-2899.
Coleman et al., "Phase II study of docetaxel in patients with liver metastases from breast cancer", Annals Oncol., 11 (2000) 541-546.
Kaye et al., "Phase II Trials of Docetaxel (Taxotere®) in Advanced Ovarian Cancer—an Updated Overview", Eur. J. Cancer, 33(13) (1997) 2167-2170.
Marur et al., "Phase II Trial of Capecitabine and Weekly Docetaxel in Metastatic Renal Cell Carcinoma", Urol., 72(4) (Oct. 2008).
McKiernan et al., "Phase I Trial of Intravesical Docetaxel in the Management of Superficial Bladder Cancer Refractory to Standard Intravesical Therapy", J. Clin. Oncol., 24(19) (Jul. 1, 2006) 3075-3080.
Okuno et al., "Small Cell Lung Cancer: Current Therapy and Promising New Regimens", Oncologist, 7 (2002) 234-238.
Rigas et al., "Docetaxel in the Treatment of Esophageal Cancer", Seminars Oncol., 32 (suppl. 4) (2005) S39-S51.
Takekida et al., "Phase II Study of Combination Chemotherapy With Docetaxel and Carboplatin for Locally Advanced or Recurrent Cervical Cancer", Int'l J. Gynecol. Cancer, 20(9) (Dec. 2010) 1563-1568.
Wikipedia, N-(2-Hydroxypropyl) methacrylamide, Accessed: Dec. 20, 2012, pp. 1-2, URL: http://en.wikipedia.org/wiki/N-(2-Hydroxypropyl)_methacrylamide.
Office Action issued in U.S. Appl. No. 12/903,927 dated Dec. 20, 2012.
Borgman et al., Targetable HPMA Copolymer-Aminohexylgeldanamycin Conjugates for Prostate Cancer Therapy; Pharm Res. Jun. 2009; 26(6): pp. 1407-1418.
Official Notice of Rejection in Japanese Patent Application No. 2015-016111, dated Nov. 17, 2015.
Smyth JF et al., Activity of docetaxel (Taxotere) in small cell lung cancer. The Early Clinical Trials Group of the EORTC, 1-1. Eur J Cancer. 1994; 30A(8):1058-60, Abstract only.
Hesketh PJ et al., Evaluation of docetaxel in previously untreated extensive-stage small cell lung cancer: a Southwest Oncology Group phase II trial, 1-1. Cancer J Sci Am. Jul.-Aug. 1999; 5(4):237-41, p. 237 only.
Izbicka E et al., Molecular determinants of differential sensitivity to docetaxel and paclilaxel in human pediatric cancer models; Anticancer Res. May-Jun. 2006; 26(3A):1983-8, Abstract only.
Nicoletti MI et al., Comparison of paclitaxel and docetaxel activity on human ovarian carcinoma xenografts, Eur J Cancer. 1994; 30A(5):691-6, Abstract only.
Dykes DJ et al., Response of human tumor xenografts in athymic nude mice to docetaxel (RP 56976, Taxotere), Invest New Drugs, 1995; 13(1):1-11, Abstract only.
Francis P et al, Phase II trial of docetaxel in patients with platinum-refractory advanced ovarian cancer, J. Clin Nov. 1994; 12(11):2301-8, Abstract only.
Piccart MJ et al, Docetaxel: an active new drug for treatment of advanced epithelial ovarian cancer, J Natl Cancer Inst. <https://www.ncbi.nlm.nih.gov/pubmed/7752272> May 3, 1995; 87(9):676-81, Abstract only.

(56) References Cited

OTHER PUBLICATIONS

Gupta D. et al., A phase II study of weekly topotecan and docetaxel in heavily treated patients with recurrent uterine and ovarian cancers, *Gynecol Oncol*, Jun. 2009;113(3):327-30. doi:10.1016/j.ygyno.2009.02.018, Abstract only.

Coleman RE et al, Phase II study of docetaxel in patients with liver metastases from breast cancer. UK study group, Ann Oncol, May 2000; 11(5)541-6, Abstract only.

Ishikawa T et al, Complete disappearance of pulmonary metastases in a case of hepatocellular carcinoma treated with docetaxel-based systemic chemotherapy, J Gastroenterol Hepatol, Dec. 2004;19(12):1423-6, Abstract only.

Pearl ML, A phase II study of weekly docetaxel for patients with advanced or recurrent cancer of the cervix, Gynecol Obstet Invest, 2007;64(4):193-8. Epub Jul. 30, 2007, Abstract only.

S. G. Arbuck et al New drugs in non-Hodgkin's lymphoma, Annals of Oncology 8 (Supp 1): S119-S128, 1997, Abstract only.

D R Budman et al, Phase II trial of docetaxel in non-Hodgkin's lymphomas: a study of the Cancer and Leukemia Group B, JCO Oct. 1997 vol. 15 No. 10 3275-3279, Abstract only.

J M Zekri et al, Phase II study of docetaxel in patients with relapsed or refractory malignant lymphoma, British Journal of Cancer (2003) 88, 1335-1338. doi:10.1038/sj.bjc.660091, Abstract only.

Otová et al, Effects of paclitaxel, docetaxel and their combinations on subcutaneous lymphomas in inbred Sprague-Dawley/Cub rats, Eur J Pharm Sci. Dec. 2006;29(5):442-50. Epub Aug. 23, 2006, Abstract only.

FDA approves Taxotere for use in combination with cisplatin and fluorouracil for the induction treatment of patients with inoperable, locally advanced squamous cell carcinoma of the head and neck, accessed May 19, 2016.

FDA Approves Docetaxel, accessed May 19, 2016.

T. P. Szatrowski et al, Phase I Trial of Docetaxel (Taxotere) for Patients with Relapsed or Refractory Acute Myeloid Leukemia (AML), Acute Leukemias VIII. vol. 40 of the series Haematology and Blood Transfusion / Hämatologie und Bluttransfusion pp. 477-481 (2001), Abstract only.

Christopher J. Logothetis, MD et al, Docetaxel in the Management of Advanced or Metastatic Urothelial Tract Cancer article/docetaxel-management-advanced-or-metastatic-urothelial-tract-cancer, Oncology Review Article | Jun. 1, 2001 | Kidney Cancer, Abstract only.

Albertsson et al, Phase II studies on docetaxel alone every third week, or weekly in combination with gemcitabine in patients with primary locally advanced, metastatic or recurrent esophageal cancer, Med Oncol. 2007; 24(4):407-12, Abstract only.

Haller DG et al, Docetaxel in advanced gastric cancer, Anticancer Drugs. Jun. 2002; 13(5):451-60, Abstract only.

Roth AD, Docetaxel-based chemotherapy in the treatment of gastric cancer, Ann Oncol, 2003;14 Suppl 2:ii41-4, Abstract only.

Maki RG, Gemcitabine and docetaxel in metastatic sarcoma: past, present, and future, Oncologist, Aug. 2007; 12(8):999-1006, Abstract only.

Vanhoefer U. et al, Comparative antitumor efficacy of docetaxel and paclitaxel in nude mice bearing human tumor xenografts thatoverexpress the multidrug resistance protein (MRP), Ann Oncol, Dec. 1997; 8(12):1221-8, Abstract only.

Zwerdling T. et al, Phase II investigation of docetaxel in pediatric patients with recurrent solid tumors: a report from the Children's Oncology Group, Cancer. Apr. 15, 2006; 106(8):1821-8, Abstract only.

York et al., "Facile Synthesis of Multivalent Folate-Block Copolymer Conjugates via Aqueous RAFT Polymerization: Targeted Delivery of siRNA and subsequent Gene Suppression", Biomacromolecules, vol. 10, No. 4, Apr. 13, 2009, pp. 936-943.

Tijerina et al, "Correlation of subcellular compartmentalization of HPMA Copolymer-Mce6 Conjugates with Chemotherapeutic Activity in Human Ovarian Carcinoma Cells", Pharmaceutical Research, vol. 20, No. 5, May 1, 2003, pp. 728-737.

Mitra et al., "Polymer-peptide conjugates for angiogenesis targeted tumor radiotherapy", Nuclear Medicine and Biology, vol. 33, No. 1, Jan. 1, 2006, pp. 43-52.

Choi et al., "Synthesis of HPMA Copolymer Containing Adriamycin Bound via an Acid-Labile Spacer and its Activity toward Human Ovarian Carcinoma Cells", Journal of Bioactive and Compatible Polymers, vol. 14, No. 2, Jan. 10, 2006, pp. 323-331.

Gao et al., "Colon-specific 9-aminocamptothecin-HPMA Copolymer conjugates containing a 1, 6-elimination spacer", Journal of Controlled Release, col. 110, No. 2, Jan. 10, 2006, pp. 323-331.

Nori et al., "Tat-Conjugated Synthetic macromolecules Facilitate Cytoplasmic Drug Delivery to Human Ovarian Carcinoma Cells", Bioconjugate Chem. col. 14, No. 1, Jan. 1, 2003, pp. 44-50.

Segal et al., "Targeting Angiogenesis-Dependent Calcified Neoplasms using Combined Polymer Therapeutics", PLoS One, Public Library of Science, vol. 4, No. 4, Apr. 1, 2009, pp. e5233.1-e5233.15.

York et al, "Advances in the synthesis of amphiphilic block copolymers via RAFT polymerization" Stimuli-responsive drug and gene delivery, Advanced Drug Delivery Reviews, vol. 60, Np., 9, Jun. 10, 2008, pp. 1018-1036.

Elivira et al., "Covalent Polymer-Drug Conjugates", Molecules, vol. 10. No. 1, Jan. 31, 2005, pp. 114-125.

Peng et al, "Spacer length impacts the efficacy of targeted docetaxel conjugates in prostate-specific membrane antigen expressing prostate cancer", Journal of Drug Targeting, col. 21, No. 10, Jan. 1, 2013, pp. 968-980.

European Search Report in European Patent Application No. EP 10 82 4024, dated Apr. 30, 2015.

Miller et al. "A novel bi-specific targeting agent based on a polymer-alendronate-taxane conjugate to target metastatic prostate carcinomas", 99th AACR Annual Meeting, Apr. 12-16, 2008, pp. 2-3.

Official Notice of Rejection in Japanese Patent Application No. 2014-213125, dated Sep. 8, 2015.

Office Action in U.S. Appl. No. 12/903,927 mailed on Jun. 7, 2012.

Duncan et al., "Anticancer agents coupled to N-(2-hydroxypropyl)methylacrylamide copolyers. II. Evaluation of daunomycin conjugates in vivo against L1210 leukaemia," Br. J. Cancer, vol. 57, pp. 147-156, 1988.

Lyseng-Williamson et al., "Docetaxel: A review of its use in metastatic breast cancer," Drugs, vol. 65, No. 17, pp. 2513, 2515, 2005.

* cited by examiner

SEQUENCE LISTING

```
<160> NUMBER OF SEQ ID NOS: 9

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Leu Gly
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Phe Phe
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Gly Val Phe
1

<210> SEQ ID NO 4
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 4

Gly Gly Val Phe
1

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Ser Ser Lys Leu Gln
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: glutaryl-4-hydroxyprolyl
<220> FEATURE:
<221> NAME/KEY: MOD_RES
<222> LOCATION: (4)..(4)
<223> OTHER INFORMATION: cyclohexaglycyl

<400> SEQUENCE: 6

Xaa Ala Ser Xaa Gln Ser Leu
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Asp Thr Arg Pro
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Pro Asp Thr Arg Pro
1               5

<210> SEQ ID NO 9
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 9

Tyr Cys Ala Arg Glu Pro Pro Thr Arg Thr Phe Ala Tyr Trp Gly
1               5                   10                  15
```

HPMA—DOCETAXEL CONJUGATES AND USES THEREFORE

This application claims priority to U.S. Provisional Application No. 61/103,390, filed Oct. 7, 2008, the contents of which are hereby incorporated by reference in their entirety.

The invention described herein was made under a joint research agreement between Rexahn Pharmaceuticals, Inc. and University of Maryland, Baltimore.

BACKGROUND OF THE INVENTION

1. Field of the Invention

The present invention is drawn to compositions comprising conjugates of an anticancer agent such as gemcitabine or docetaxel and/or a targeting ligand such as RGDfK, EPPT1 peptide or folate to N-(2-hydroxypropyl)methacrylamide (HPMA), and with methods for delivering those conjugates to a cell utilizing said compositions.

2. Background of the Invention

Docetaxel (Taxotere®) is a member of one of the most important new classes of oncology drugs. However, its poor solubility presents pharmaceutical challenges, and emerging data suggest that specific tissue exposure profiles, such as low drug concentrations for extended times, can enhance beneficial antitumor mechanisms. As the main disadvantage of docetaxel is that it is highly lipophilic and practically insoluble in water, formulation considerations for docetaxel have been studied extensively. For clinical use, it is formulated and administered in a cosolvent system. The drug is packaged at 40 mg/ml in polysorbate-80 (USPDI). Prior to use, it is diluted to 10 mg/ml with a solution containing 13% (v/v) ethanol in water. Before administration, the drug is further diluted in 250 ml saline or dextrose, achieving a final concentration of 0.3-0.9 mg/liter. The solution is used within 4 h. Some apparently unique adverse effects are associated with docetaxel formulation. Delayed-onset pleural effusions and edema have led in some cases to the discontinuation of treatment. Because of the toxicities associated with the cosolvents required for taxane administration, a variety of alternative compositions of docetaxel including synthesis of docetaxel analogues, entrapment in liposomes and preparation of polymer-docetaxel conjugates have been investigated. With respect to the preparation of polymer-docetaxel conjugates, some polymers have been proposed including poly(amino acid)s (WO/2007/067417) and synthetic polymers such as poly(ethylene glycol) (PEG).

In the past few years, gemcitabine (Gemzar®), a novel pyrimidine nucleoside analogue, has become the standard chemotherapeutic agent used in patients with pancreatic cancer. Pancreatic adenocarcinoma is the fourth leading cause of cancer death in the United States. Nationwide, 28,000 new cases are diagnosed annually. Chemotherapy and radiation therapy are largely ineffective, and metastatic disease frequently develops even after potentially curative surgery. The 1-year survival rate of this cancer is 20%, and the 5-year survival rate is only 1-3%. Not more than 25% of patients with pancreatic cancer will benefit from gemcitabine. Clearly, an effective treatment for this devastating disease is urgently needed. To increase the benefit of gemcitabine in cancer patients, the new and first formulation of polymer-gemcitabine conjugate is disclosed in this invention.

In light of the foregoing, there is a high unmet need in the art for modifications of docetaxel and gemcitabine that can retain or increase its activity with tumor specificity while reducing its toxicity.

SUMMARY OF THE INVENTION

Figure 1:
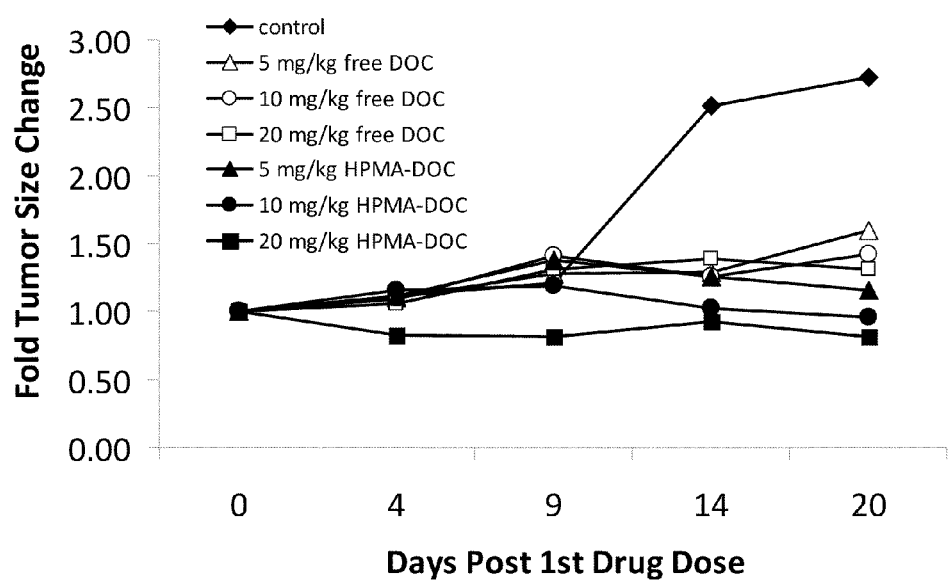
FIG. 1 is a graph showing the inhibition of tumor growth by HPMA-GFLG-docetaxel (DOC) conjugates in nude mice subcutaneously injected with Mia-Paca human pancreatic carcinoma cells. The efficacy is expressed as fold change in tumor size as a function of time (days).

The present invention relates to conjugates of an anticancer agent such as gemcitabine or docetaxel and/or a targeting ligand such as RGDfK, EPPT1 peptide or folate to water-soluble polymer, poly N-(2-hydroxylpropyl)methacrylamide (HPMA) and use of those conjugates as specific intracellular carriers of docetaxel or gemcitabine into tumor vessels. The present invention further relates to use of those conjugates to lower the toxicity of docetaxel or gemcitabine and to methods of treating cancer.

In a certain embodiment, the anticancer agent is docetaxel or gemcitabine.

In another embodiment, the composition further comprises a lysosomally degradable amino acid sequence and oligopeptides including but not restricted to Gly-Phe-Leu-Gly (SEQ ID NO: 1), Gly-Ile-Phe, Gly-Val-Phe, Gly-Gly-Phe, Gly-Gly-Phe-Phe (SEQ ID NO: 2), Gly-Ile-Tyr, Phe, Gly, Gly-Gly, Ala, Ser, Gly-Phe, Gly-Leu-Phe, Gly-Phe-Phe, Gly-D-Phe-Phe, Ala-Gly-Val-Phe (SEQ ID NO: 3), Gly-Gly-Val-Phe (SEQ ID NO: 4), Gly-Phe-Tyr, Gly-B-Ala-Tyr. Gly-Leu, Gly-Phe-Gly, His-Ser-Ser-Lys-Leu-Gln (SEQ ID NO: 5) and glutaryl-4-hydroxyprolyl-Ala-Ser-cyclohexaglycyl-Gln-Ser-Leu (SEQ ID NO: 6).

In a further embodiment, the composition comprises targeting peptides such as RGDfK, EPPT1 peptide or folate to HPMA copolymer-docetaxel or HPMA copolymer-gemcitabine. In such an instance, the targeting system includes covalently attaching a targeting ligand such as RGDfK, EPPT1 peptide, or folate to the polymer.

Still another embodiment of the invention comprises the weight average molecular weight ($M_w$) of HPMA copolymer-drug conjugates ranging from about 10 kDa to about 250 kDa, from about 20 kDa to about 170 kDa, from about 50 kDa to about 250 kDa, or from about 100 kDa to about 170 kDa. Other embodiments of the invention comprises the weight average molecular weight ($M_w$) of HPMA copolymer-drug conjugates of at least about 20 kDa, at least about 50 kDa, at least about 100 kDa, at least about 125 kDa or at least about 150 kDa.

In certain embodiments, therefore, the present invention is characterized by high molecular weight HPMA copolymer-drug conjugates with or without a targeting ligand. High molecular weight HPMA copolymer-drug conjugates provide advantages not suggested by current drug polymer conjugates. For example, high molecular weight HPMA copolymer-drug conjugates possess a longer plasma half life ($t_{1/2}$) resulting in longer circulation in the bloodstream.

Because the polymer chains are longer there is more drug attached on each polymer chain, even if there is a similar degree of drug incorporation. Thus, the use of high molecular weight HPMA copolymer-drug conjugates can provide a higher amount of drug being delivered to the tumor site.

Further, the attachment of a targeting ligand or moiety to a polymer-drug conjugate results in enhanced specificity of the drug to tumor cells. In some embodiments, the targeting ligand can be RGDfK, EPPT1, or folate. This effect, combined with the passive tumor accumulation of high molecular weight HPMA copolymer-drug conjugates, results in high therapeutic effect by increasing tumor specificity, improving stability and reducing toxicity. Thus this system has great potential in the delivery of therapeutic agents for the treatment of cancer.

Another embodiment of the present invention provides a method for delivering a therapeutic agent, comprising administering to a subject an effective amount of docetaxel or gemcitabine that is conjugated to HPMA copolymers.

Yet another embodiment of this invention provides methods for delivering a therapeutic agent to a cell utilizing compositions comprising HPMA copolymer conjugated to docetaxel or gemcitabine.

DETAILED DESCRIPTION OF THE INVENTION

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. All references cited herein are incorporated by reference as if each had been individually incorporated.

Polymer-Based Therapeutics

Free anticancer drugs diffuse throughout a cell and are not concentrated at a specific subcellular location. In addition, if such drugs are administered intravenously they are systemically distributed to all tissues of the body. The action of these drugs at these unintended sites of distribution results in observable systemic side effects. It is thus preferred to localize the drug to the sites in the body where the action is desired. Targeting these agents to the subcellular site where they are most effective increases their efficacy and decreases their toxicity.

Targeting of anticancer drugs to tumors can be achieved by "passive targeting" and "active targeting". Passive targeting is achieved by incorporation or attachment of anticancer drugs into macromolecular carriers such as water-soluble polymers. Active targeting is achieved by incorporating cellular targeting moieties that are specific to recognition molecules (receptors) on the surface of the cancer cells.

Polymers localize preferentially in solid tumors when compared to normal tissue. This occurs due to a phenomenon called the Enhanced Permeability and Retention ("EPR") effect, which is attributed to morphological changes in tumor tissue, where the leaky vasculature produced due to neoangiogenesis results in the leakage of vascular contents into the extracellular tissue. In addition, the lymphatics may be blocked, which results in the accumulation of macromolecular agents in the extracellular tissue surrounding tumor cells. This phenomenon can be used to target tumor cells by attaching drugs to the polymers. Since polymers localize around tumor cells, the drugs attached to the polymers are also available at higher concentrations around the tumor. Drugs attached to polymers are taken inside cells by endocytosis. However, since the drugs remain covalently attached to the polymer backbone, they may not be as effective as free drugs. This may be overcome by the use of biodegradable or hydrolysable peptide sequences to link the drug to the polymer backbone. The sequences that are chosen are such that they can be degraded inside the cell under specific conditions.

Polymer-based therapeutics have a large hydrodynamic volume, which translates into a longer intravascular half-life. Polymer-based therapeutics also enhance the solubility and the bioavailability of insoluble drugs. Other advantages afforded by polymer-based therapeutics include increased maximum tolerated dose, decreased non-specific toxicity, enhanced induction of apoptosis, and activation of alternate signaling pathways (Kopecek et al., Advances in Polymer Science, 122 (Biopolymers II): 55-123 (1995)).

In addition, cancer cells often have surface molecules that are either absent in normal tissue or over-expressed in comparison to the normal tissue. These may include growth factor receptors and/or certain antigens. Attaching recognition molecules to polymers that bind to these molecules results in a high concentration of polymers in the local environment of the tumor. Such targeting moieties include antibodies and peptidyl ligands for cell surface receptors. Receptor mediated endocytosis initiated by the binding of some of these recognition molecules to their receptors can result in an increased intracellular concentration and correspondingly an enhanced therapeutic effect.

Several polymer-drug conjugates in clinical trials include HPMA-copolymer-based or PGA-based conjugates. HPMA copolymers are biocompatible, non-immunogenic and non-toxic carriers that enable specific delivery into tumor cells overcoming limitations of drug-related toxicities (Duncan, et al., Hum. Exp. Toxicol., 17: 93-104 (1998)). Moreover, their body distribution is well characterized and they are known to accumulate selectively in the tumor site due to the enhanced permeability and retention (EPR) effect. The conjugate can also include a targeting ligand to direct to sites of endothelial cell proliferation or cancer cells or to specific receptors or markers associated with proliferating cells. There are currently two polyglutamate-drug conjugates and six HPMA copolymer-drug conjugates at various stages of clinical trials and further polymer-drug conjugates including dextran-drug conjugates and PEG-drug conjugates are reported in clinical or preclinical development.

The compounds of the present invention possess these attributes, increasing the delivery of anticancer agents, in addition, the disclosed compositions enhance both targeting to a specific cell type as well as uptake by the targeted cancer cells relative to other targeting strategies for anticancer drugs.

B. Compounds

As used herein, the term "HPMA" means the compound N-(2-hydroxypropyl) methacrylamide, which is a hydrophilic polymer represented by the following structure:

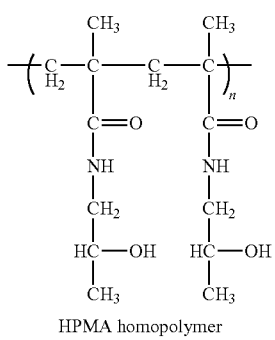

HPMA homopolymer

The "anticancer agent" of the invention, in particular embodiments, is docetaxel or gemcitabine.

The present invention is advantageous over other HPMA-drug conjugates in several ways:

First, the molecular weight of conjugates according to the present invention is larger than the clinically evaluated HPMA drug conjugates. The known HPMA copolymer-drug conjugates in pre-clinical or clinical trials have a molecular weight of ~25-50 kDa whereas certain embodiments of the present invention are drawn to HPMA having a molecular weight range of ~100-170 kDa. Increased molecular weight HPMA conjugates have a longer plasma residence time and an increase in passive tumor targeting by enhanced EPR. Other embodiments of the invention have weight average molecular weights ($M_w$) of HPMA copolymer-drug conjugates ranging from about 10 kDa to about 250 kDa, from about 20 kDa to about 170 kDa, from about 50 kDa to about 250 kDa, or from about 100 kDa to about 170 kDa. Still other embodiments of the invention comprises the weight average molecular weight ($M_w$) of HPMA copolymer-drug conjugates of at least about 20 kDa, at least about 50 kDa, at least about 100 kDa, at least about 125 kDa or at least about 150 kDa. High molecular weight drug-polymer conjugates can be obtained using the synthetic methods disclosed herein.

In addition to increased circulation times, the use of high molecular weight conjugates can provide increased drug delivery to a specific site. In particular, in cases where the degree of drug incorporation (on a percentage or mole percentage basis) is similar in low and high molecular weight species, a single polymer chain will have a higher number of drug molecules than a lower molecular weight chain. Thus, more drug will be delivered to a specific location or tumor when using a high molecular weight chain that when a low molecular weight chain is used. This results in an essentially higher local concentration of drug in the vicinity of the tumor.

Second, another novelty of the present invention is to prepare a second-generation of HPMA-docetaxel or gemcitabine conjugates containing tumor specific targeting ligand, for example, RGDfK, EPPT1 peptide or folate. Generally with passively targeted HPMA conjugates success in clinical trials has been marginal, primarily because of the limited accumulation of the drug in solid tumors by passive diffusion alone and heterogeneity of clinical presenting cancers. Active targeting strategies allow targeting to multiple cell types taking into account the variations in tumor physiology, maximize distribution in the microenvironment of solid tumors while concurrently minimizing their non-specific uptake in other organs. Active targeting strategies can also significantly improve the therapeutic efficacy by (1) increasing tumor specificity; (2) improving pharmacokinetics; and (3) reducing toxicity. Several such strategies have emerged over the recent years that can be exploited to significantly improve tumor localization of anticancer drugs. Active targeting of polymeric drug delivery systems by attaching molecular markers (e.g., peptides and antibodies) has been shown to significantly improve tumor localization.

Mucin-1 is a transmembrane molecule, expressed by most glandular epithelial cells. Several important features make mucin-1 an attractive receptor for targeted delivery to tumors.

First, mucin-1 is overexpressed on almost all human epithelial cell adenocarcinomas, including 90% of human breast, ovarian, pancreatic, colorectal, lung, prostate, colon, and gastric carcinomas. Moreover, mucin-1 expression has been demonstrated in nonepithelial cancer cell lines (astrocytoma, melanoma, and neuroblastoma), as well as in hematological malignancies such as multiple myeloma and some B-cell non-Hodgkin lymphomas, in total constituting 50% of all cancers in humans.

Second, in adenocarcinomatous tissue, as the result of the lost gland architecture, mucin-1 is ubiquitously expressed all over the cell surface. Because of its rod-like structure, the molecule extends 100-200 nm above the surface, which is 5-10-fold the length of most membrane molecules. This feature makes mucin-1 an accessible target for therapeutic probes.

Third, whereas in normal tissues mucin-1 is heavily glycosylated (50-90% of its molecular mass is due to carbohydrates), mucin-1 is underglycosylated in neoplastic tissues. Reduced glycosylation permits the immune system to access the peptide core of the tumor-associated underglycosylated mucin-1 antigen and reveals epitopes, which in the normal cell are masked. This feature makes it possible to design probes that discriminate between normal cells and adenocarcinoma cells.

Fourth, the extracellular domain of mucin-1, defined by the presence of the PDTRP (SEQ ID NO: 7) sequence, extends above the cell surface, thus interfering with the interaction between adhesion molecules on the tumor cell surface and their ligands on lymphocytes, aiding in the inaccessibility of tumor epitopes to immune recognition. Therefore, there is no tendency for tumor antigen down-regulation in response to immunotherapy, and mucin-1 expression remains homogeneously up-regulated during the life of the tumor and tumor metastases. These features are important in designing targeted drug delivery for different stages of tumor progression.

A number of investigations have focused on the potential to use mucin-1 as a target for immunotherapy. Multiple monoclonal antibodies have been produced to recognize the immunogenic APDTRP (SEQ ID NO: 8) sequence of the tandem repeat. However, when antibodies were used as targeting molecules, the immunogenicity and long plasma half-life of these proteins were detrimental. Consequently, the use of small peptides can eliminate these shortcomings because peptide ligands are nonimmunogenic and have high affinity and selectivity for receptors. A synthetic peptide designated EPPT1 (YCAREPPTRTFAYWG (SEQ ID NO: 9), has been developed as a specific ligand and has shown significant affinity (Kd=20 µM). EPPT1, labeled with (99 mTc), has been used to image breast carcinomas in vivo. All of the features of the mucin-1 protein listed above make EPPT1 an ideal candidate for use as a tumor targeting ligand.

A number of tumor cell and associated vasculature specific receptors have also been identified that differentiate tumor cells from normal cells. The $\alpha V\beta 3$ integrin is one of the most studied and is selectively overexpressed in tumor associated neovasculature as well as in certain metastatic cancers (Felding-Habermann et al., Clin. Exp. Metastasis, 19: 427-436 (2002)). High affinity αVβ3 selective ligands containing the tripeptide sequence, Arg-Gly-Asp (RGD), have been identified by phage display studies. The conformationally restrained RGD sequence, i.e. cyclic RGD, contains disulfide bridges and binds to αVβ3 20-40 fold more avidly than linear RGD peptides (Koivunen, E., Wang, B. & Ruoslahti, E., Biotechnology (N.Y.), 13: 265-270 (1995)). RGD peptide has been conjugated with doxorubicin (Arap, W., Pasqualini, R. & Ruoslahti, E., Science, 279: 377-380 (1998)) for targeted chemotherapy as well as for targeted radiotherapy (Capello, A. et al., J. Nucl. Med., 45: 1716-1720 (2004)). They have been conjugated to humanized antibodies, liposomes, poly (ethylene glycol) and HPMA copolymers to improve biodistribution and increase tumor accumulation and antitumor efficacy. These studies make RGD an ideal targeting ligand for studying anti-tumor drug targeting.

Folic acid, its salts, and/or its reduced counterparts (collectively referred to as "folates") are required by eukaryotic cells for one carbon transfer reactions used in the biosynthesis of nucleotide bases. Cellular uptake of folates is facilitated by either a low affinity reduced folate carrier (Km~1 µM), which is present in many cells of the body, or a high affinity glycosylphosphatidylinositol-linked folate receptor (FR) (KD=~100 pM), which exhibits highly limited distribution. FRs exhibit limited expression on healthy cells, but are often present in large numbers on cancer cells. For example, FRs are overexpressed on epithelial cancers of the ovary, mammary gland, colon, lung, prostate, nose, throat, and brain. FRs are also overexpressed on hematopoietic malignancies of myeloid origin, including chronic and acute myelogenous leukemias. A strong correlation has been observed between FR expression and the grade and histological stage of a tumor. A variety of folate linked molecules and complexes have been designed to enable selective delivery of drugs to FRs on cancer cells and activated macrophages. Other features that render folic acid an attractive ligand for use in drug targeting include its low molecular weight (MW 441), water solubility, stability to diverse solvents, pH, and heat, facile conjugation chemistry, lack of immunogenicity, and high affinity for its receptor.

Disclosed herein are compounds that can be used, for example, in anticancer therapies. These compounds typically increase or alter the targeted delivery of anticancer compounds or other therapeutic compounds. These compounds can include an anticancer agent, a carrier molecule, an optional linker molecule, and, optionally, a targeting ligand. In certain embodiments, the linker may be an oligopeptide, such as, for example, Gly-Phe-Leu-Gly (SEQ ID NO: 1). In certain embodiments, the targeting ligand may be, for example, RGDfK, EPPT1 or folate.

Also disclosed herein are compounds including an anticancer agent, a carrier molecule, optionally a linker molecule, optionally a targeting ligand, wherein the anticancer agent, the carrier molecule, the linker molecule, and the targeting ligand are attached to one another via one or more covalent bonds.

There are a number of different ways the anticancer agent, the carrier molecule, the optional linker molecule and the optional targeting ligand can be attached to one another. In certain embodiments, the anticancer agent, the carrier molecule, and optionally a linker molecule and optionally a targeting ligand can be directly attached to one another. In other embodiments, the anticancer agent is attached to the carrier molecule via a covalent bond, or alternatively via a linker molecule.

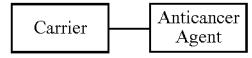

In other embodiments, a linker molecule is directly attached to the carrier molecule via a covalent bond, and the anticancer agent is directly attached to the linker molecule.

In other embodiments, an anticancer agent is directly attached to the carrier molecule via a covalent bond, and a targeting ligand is directly attached to the carrier molecule via a covalent bond.

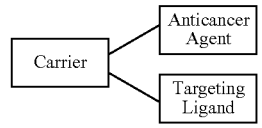

In other embodiments, a linker molecule is directly attached to the carrier molecule via a covalent bond, and the anticancer agent is directly attached to the linker molecule, and a targeting ligand is directly attached to the carrier molecule via a covalent bond.

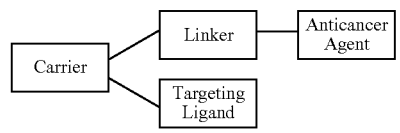

In other embodiments a linker molecule is directly attached to the carrier molecule via a covalent bond, and a targeting ligand is directly attached to the linker molecule, and an anticancer agent is directly attached to the carrier molecule via a covalent bond.

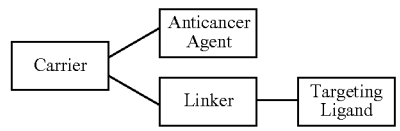

In other embodiments, a linker molecule is directly attached to the carrier molecule via a covalent bond, and the anticancer agent is directly attached to the linker molecule, and a targeting ligand is directly attached to a different linker molecule, which is directly attached to the carrier molecule via a covalent bond.

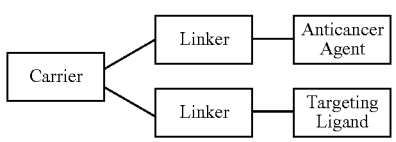

The anticancer agent, the carrier molecule, the linker molecule and the target ligand used to produce the compounds are discussed below.

1. Anticancer Agent

An "anticancer agent" means any agent useful to combat cancer. Any anticancer agent may be used that can be directly or indirectly attached to the carrier molecule and/or the linker. A partial list of anticancer agents that can be used with the disclosed compositions can be found in, for example, U.S. Pat. No. 5,037,883, which is herein incorporated by reference as well as any publications and patents, or patent applications, cited therein which contain anticancer agents. U.S. Pat. Nos. 6,348,209, 6,346,349, and 6,342,221 also describe agents related to anticancer compounds. Classes of anticancer agents include, but are not limited to, chemotherapeutic agents, cytotoxins, antimetabolites, alkylating agents, protein kinase inhibitors, anthracyclines, antibiotics, antimitotic agents (e.g. antitubulin agents), corticosteroids, radiopharmaceuticals, and proteins (e.g. cytokines, enzymes, or interferons). Specific examples include, but are not limited to docetaxel, gemcitabine, imatinib (Gleevec®), 5-fluorouracil, 9-aminocamptothecin, amine-modified geldanamycin, doxorubicin, paclitaxel (Taxol®), procarbazine, hydroxyurea, meso e-chlorin, cisplatin, Gd(+3) compounds, asparaginase, and radionuclides (e.g I-131, Y-90, In-111, and Tc-99m). There are many anticancer agents known in the art and many continue to be developed.

One of ordinary skill will be able to make the necessary chemical modifications of the anticancer agent for attaching the anticancer agent to the carrier molecule or linking molecule based on the description below.

2. Carrier Molecule

Any carrier molecule can be used. Typically carrier molecules will be polymer molecules. Typically the carrier polymer molecule is a large macromolecule of at least about 5,000 daltons. In other embodiments, the carrier molecule is at least about 25,000 daltons, at least about 50,000 daltons, at least about 100,000 daltons, at least about 125,000 daltons or at least about 150,000 daltons. The carrier molecule can range from about 5,000 daltons to about 25,000 daltons, or from about 25,000 daltons to about 100,000 daltons, or from about 50,000 daltons to about 130,000 daltons, or from about 100,000 daltons to about 170,000 daltons, or from about 120,000 daltons to about 200,000 daltons, or from about 120,000 daltons to about 1,000,000 daltons. The carrier molecule aids in the transport of an anticancer agent across the cell membrane. Thus, when the anticancer agent is directly or indirectly attached to the carrier molecule it typically crosses a cell membrane better than the anticancer agent alone. There are numerous carriers and macromolecular carriers known in the art that will function as the carrier molecule. Examples of carrier molecules are also described in U.S. Pat. No. 5,258,453 for "Drug delivery system for the simultaneous delivery of drugs activatable by enzymes and light;" U.S. Pat. No. 5,037,883 for "Synthetic polymeric drugs;" U.S. Pat. No. 4,074,039 for "Hydrophilic N,N-diethyl acrylamide copolymers;" U.S. Pat. No. 4,062,831 for "Copolymers based on N-substituted acrylamides, N-substituted methacrylamides and N,N-disubstituted acrylamides and the method of their manufacturing;" U.S. Pat. No. 3,997,660 for "Soluble hydrophilic polymers and process for producing the same;" U.S. Pat. No. 3,931,123 for "Hydrophilic nitrite copolymers;" and U.S. Pat. No. 3,931,111 for "Soluble hydrophilic polymers and process for processing the same" each of which is individually and specifically herein incorporated by reference in its entirety.

In one embodiment, the carrier molecule comprises a polymer produced by the polymerization of an unsaturated monomer. Examples of monomers include, but are not limited to, acrylates and methacrylates. In one embodiment, the carrier molecule is a copolymer produced from the polymerization of N-(2-hydroxypropyl)methacrylamide (HPMA comonomer) with drug—or targeting moiety—or imaging agent containing comonomers. The resulting polymer-drug conjugates are referred to herein as HPMA copolymers.

Polymers prepared according to the invention can have a polydispersity of from about 1.0 to about 2.0. In exemplary embodiments, the polydispersity is from about 1.3 to about 1.8, from about 1.3 to about 1.5 or from about 1.5 to about 1.7. Some embodiments have a polydispersity of about 1.4, while other embodiment can have a polydispersity of about 1.7.

3. Linker Molecule

A "linker" refers to a group that spatially separates drug or a targeting ligand from the carrier molecule. The linker can be any sort of entity, such as, without limitation, a poly(ethylene glycol), an amino acid, poly(amino acid) (e.g. a peptide or oligopeptide), or polypeptide (e.g. a protein), one end of which is capable of forming a covalent bond with the carrier molecule and the other end of which is capable of forming a covalent bond with a drug or a targeting ligand. The linkers may also include short peptides with specific sequences susceptible to lysosomal degradation, such as Gly-Phe-Leu-Gly (SEQ ID NO: 1). Other examples include, for prostate cancer, linkages targeted to prostate cells and to a prostate-specific antigen (PSA) having sequence-specific proteolytic capabilities. For example, PSA hydrolyzes His-Ser-Ser-Lys-Leu-Gln (SEQ ID NO: 5) and glutaryl-4-hydroxyprolyl-Ala-Ser-cyclohexaglycyl-Gln-Ser-Leu (SEQ ID NO: 6).

The linkers are typically cleavable so that the anticancer agent can be released, for example, under reducing conditions, oxidizing conditions, or by hydrolysis of an ester, amide, hydrazide, or similar linkage that forms the covalent bond between the linker and the anticancer agent. Additionally, the type of linker may augment the selective cytotoxicity (and thus improve the therapeutic index) aspect by permitting selective release of the anticancer agent adjacent to or inside the cells.

4. Targeting Ligand

The term "targeting ligand" means a molecule which serves to deliver the compound of the invention to a specific site for the desired activity, i.e. it provides localization of the compound. The localization is mediated by specific recognition of molecular determinants, molecular size of the targeting agent or conjugate, ionic interactions, hydrophobic interactions, and the like. Other mechanisms of targeting an agent to a particular tissue or region are known to those of skill in the art. Targeting ligands include, for example, molecules that bind to molecules on a targeted cell surface. Exemplary targeting ligands include antibodies, antibody fragments, small organic molecules, peptides, peptoids, proteins, polypeptides, oligosaccharides, transferrin, HS-glycoprotein, coagulation factors, serum proteins, beta-glycoprotein, G-CSF, GM-CSF, M-CSF, EPO, and the like. In exemplary embodiments of the present invention, the targeting system includes covalently attaching a targeting ligand such as RGDfK, EPPT1 peptide, or folate to the carrier molecule, linker, or anticancer agent.

5. Efficiency and Specificity of Uptake by the Cells

The compounds described herein can be characterized in that they allow for the uptake of anticancer agents by cells using typically different mechanisms than used by the anticancer agent alone. There are many ways to determine whether the efficiency and/or specificity of the uptake are increased by the carrier molecule. Typical increases of efficiency and/or specificity can be greater than or equal to at least 2 fold, 5 fold, 10 fold, 25 fold, 50 fold, 100 fold, 500 fold, 1000 fold, 5,000 fold or 10,000 fold.

C. Method of Making Compounds

The compounds of the invention can be prepared using techniques known in the art. As described, there are up to four components used to produce the compounds: the anticancer agent, the carrier molecule, the optional targeting ligand and the optional linker molecule. In particular embodiments, the compounds of the invention include a carrier molecule, an anticancer agent, a targeting ligand, and at least one linker molecule. Any of the components previously described can be reacted with one another in any possible combination or order to produce the compounds of the invention. It is sometimes preferred to couple (i.e., react) two of the components together to produce a new reaction product or intermediate, and then chemically connect the intermediate with the next component. For example, the anticancer agent can react with the carrier molecule to produce an anticancer/carrier molecule. Similarly, the anticancer agent can react with a linker molecule to produce an anticancer/linker molecule, or a linker molecule can react with the carrier molecule to produce a linker/carrier molecule. Each of these intermediates can then be reacted with an individual component (e.g., the reaction of anticancer/linker with carrier molecule to produce carrier/linker/anticancer agent) or, alternatively, each of the intermediates can react with one another to produce the compound (e.g., reaction of anticancer/linker molecule with the anticancer/carrier molecule).

In one embodiment, the compound can be produced by (1) reacting the linker with a monomer used to prepare the carrier molecule to produce a monomer/linker molecule, (2) reacting the monomer/linker molecule with anticancer agent to produce a monomer/linker/anticancer agent, and (3) polymerization of the monomer/linker/anticancer agent with at least one comonomer. In certain embodiments, the at least one comonomer is HPMA comonomer.

In other embodiments, the compound can be produced by (1) reacting the linker with a monomer used to prepare the carrier molecule to produce a monomer/linker molecule, (2) reacting the monomer/linker molecule with anticancer agent to produce a monomer/linker/anticancer agent, (3) polymerization of the monomer/linker/anticancer agent with at least one comonomer, and (4) reacting a targeting ligand with the copolymer. In such embodiments, the at least one comonomer includes a reactive site that can react with the targeting ligand. In certain embodiments, the at least one comonomer is HPMA comonomer. In other embodiments, the at least one comonomer includes HPMA comonomer and a second comonomer having a leaving group that may be displaced by the targeting ligand.

In one exemplary embodiment, the compound can be produced by (1) reacting methacryloyl chloride (MACl) with Gly-Phe (GF) and coupling the product with Leu-Gly (LG) to produce an MA-GFLG-OH molecule; (2) reacting the MA-GFLG-OH molecule with gemcitabine or docetaxel to produce the MA-GFLG-anticancer molecule; (3) reacting the MA-GFLG-anticancer molecule with the HPMA comonomer to produce HPMA copolymer-drug conjugates. This process is described in detail in Examples 1-2 to 1-8 below. 'GFLG' is disclosed as SEQ ID NO: 1.

In another exemplary embodiment, MA-GFLG-OH is reacted with Docetexal (DCT) to give MA-GFLG-DCT or Gemcitabine (GEM) to give MA-GFLG-GEM. Then, HPMA comonomer is copolymerized with MA-GFLG-DCT or MA-GFLG-GEM and another comonomer containing a leaving group, such as methacryloyl-glycylglycine-p-nitrophenylester (MA-GG-ONp, shown in Scheme 6, below) to produce HPMA-GFLG-drug-GGONp. HPMA-GFLG-drug-GGONp is then reacted with a targeting ligand to produce HPMA-GFLG-drug-targeting ligand. In certain embodiments, the targeting ligand may be, for example, RGDfK, EPPT1 peptide or folate. This process is described in detail in Examples 1-9 to 1-12 below. 'GFLG' is disclosed as SEQ ID NO: 1.

As described above, the anticancer agent, carrier molecule, and linker can be attached to one another directly or indirectly. In addition, the attachment of each component to one another can vary depending upon the types of components selected and the order in which the components are permitted to react with one another.

D. Method of Using Compounds

The disclosed compounds can be used for targeted delivery of anticancer agents to cells. The compounds disclosed herein may be administered in pharmaceutically acceptable forms and in effective amounts to a subject in need of delivery of the anticancer agent or a similar compound. The subject can, for example, be a mammal, such as a mouse, rat, rabbit hamster, dog, cat, pig, cow, sheep, goat, horse, or primate, such as monkey, gorilla, orangutan, chimpanzee, or human.

The conjugated anticancer agents disclosed herein can be used for inhibiting cancer cell proliferation. Inhibiting cancer cell proliferation means reducing or preventing cancer cell growth. Inhibitors can be determined by using a cancer cell assay. For example, either a cancer cell line can be cultured on 96-well plates in the presence or absence of the conjugated anticancer agent or anticancer agent alone or anticancer agent prepared differently then the disclosed compositions (for example, just anticancer agent and carrier) for any set period of time. The cells can then be assayed. In certain embodiments the conjugated anticancer compounds are those that will inhibit 10% or 15% or 20% or 25% or 30% or 35% or 40% or 45% or 50% or 55% or 60% or 65% or 70% or 75% or 80% or 85% or 90% or 95% of growth relative to any of the controls as determined by the assay. Other embodiments include compositions which inhibit metastatic tumor formation. Such compositions may reduce metastatic tumor formation by at least 10% or 15% or 20% or 25% or 30% or 35% or 40% or 45% or 50% or 55% or 60% or 65% or 70% or 75% or 80% or 85% or 90% or 95% of a control compound.

In certain embodiments, the compounds disclosed can be used to treat a variety of disorders that require the delivery of anticancer or similar agents. In certain embodiments, the disclosed compositions can be used to treat diseases where uncontrolled cellular proliferation occurs, such as cancers. As used herein, "treat" or "treating" means to inhibit, reduce, modulate, ameliorate, or block at least one symptom that characterizes a pathologic condition, in a subject threatened by, or afflicted with, the condition. A non-limiting list of different types of cancers is as follows: carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, metastatic cancers, or cancers in general. Specific examples of cancers that the disclosed compositions can be used to treat include B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Compounds disclosed herein may also be used for the treatment of precancer conditions such as cervical and anal dysplasias, other dysplasias, severe dysplasias, hyperplasias, atypical hyperplasias, and neoplasias.

E. Dosages

The dosage ranges for the administration of the compounds are those large enough to produce the desired effect in which delivery occurs. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary from about 1 mg/kg to 30 mg/kg in one or more dose administrations daily, for one or several days.

F. Pharmaceutically Acceptable Carriers

Any of the compounds can be used therapeutically in a pharmaceutical composition in combination with one or more pharmaceutically acceptable carriers.

Pharmaceutical carriers are known to those skilled in the art. These most typically would be standard carriers for administration of compositions to humans, including solutions such as sterile water, saline, and buffered solutions at physiological pH. Other compounds will be administered according to standard procedures used by those skilled in the art.

Molecules intended for pharmaceutical delivery may be formulated in a pharmaceutical composition. Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions that may also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions as described herein can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

G. Pharmaceutical Compositions

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

Injectable preparations, including, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

While the compounds of the invention can be administered as the sole active pharmaceutical agent, they can also be used in combination with one or more therapeutic agents, such as immunomodulators, antiviral agents or antiinfective agents.

The foregoing is merely illustrative of the invention and is not intended to limit the invention to the disclosed compounds. Variations and changes that are obvious to one skilled in the art are intended to be within the scope and nature of the invention which are defined in the appended claims. From the foregoing description, one skilled in the art can easily ascertain the essential characteristics of this invention, and without departing from the spirit and scope thereof, can make various changes and modifications of the invention to adapt it to various usages and conditions.

EXAMPLES

The invention may be further clarified by references to the following examples, which serve to exemplify some of the preferred embodiments, and not to limit the invention in any way.

Example 1

Synthesis of HPMA-Gemcitabine or Docetaxel Conjugates for Drug Delivery

HPMA comonomer drug conjugates was synthesized by the polymerization of HPMA monomer and an activated MA-GFLG-drug (SEQ ID NO: 1) comonomer at different molar ratios.

1) Synthesis of HPMA Comonomers

Synthesis of the HPMA monomer was performed as previously described (Kopecek and Bazilova, Eur. Polym. J., 9:7-14 (1973)) as shown in Scheme 1. MA-GG-ONp comonomer was made by the modified multistep procedure (Kopecek et al., Ann. N Y Acad. Sci., 446:93-104 (1985).

Scheme 1

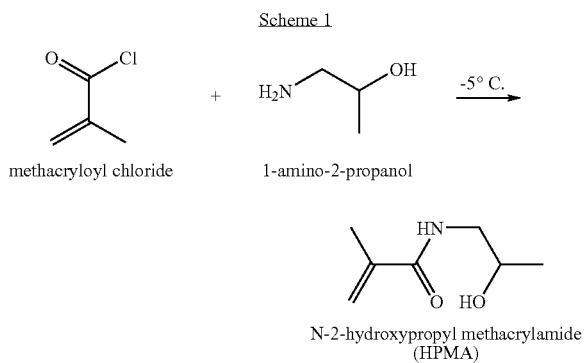

methacryloyl chloride   1-amino-2-propanol

N-2-hydroxypropyl methacrylamide (HPMA)

To a solution of 1-amino-2-propanol (65.6 ml, 0.84 mol) in 250 ml of acetonitrile, freshly distilled methacryloyl chloride (MACl) (41 ml, 0.42 mol) in 20 ml of acetonitrile was added dropwise under vigorous stirring at −5° C. A small amount of inhibitor, tertiary octyl pyrocatechine, was added to the solution. The reaction mixture was stirred for an additional 30 min at room temperature. 1-amino-2-propanol hydrochloride formed as a byproduct was precipitated and filtered off. The residue was washed with pre-cooled acetonitrile. The filtrate was cooled to −70° C. and the HPMA precipitated. After equilibrating to room temperature the product was filtered off and washed with pre-cooled acetonitrile. Recrystallization was from acetone and the pure product was isolated (melting point: 67-69° C.). MS (ESI) m/z 144 (M+1). $^1$H NMR (400 MHz, CDCl$_3$): δ 1.20 and 1.22 (d, J=6.4 Hz, 3H)), 1.97 (s, 3H), 3.18-3.21 (m, 1H), 3.48-3.51 (m, 1H), 3.95-3.96 (m, 1H), 5.36 (s, 1H), 5.74 (s, 1H).

2) Synthesis of MA-GF-OH

Methacryloylglycylphenylalanine (MA-GF-OH) was made from the reaction of methacryloyl chloride (MACl) and glycylphenylalanine (GF) as outlined in Scheme 2.

Glycylphenylalanine (Gly-Phe, 5.0 g, 22.5 mmol) was dissolved in 5.6 ml of 4N NaOH (22.5 mmol) and cooled to 0-5° C. Freshly distilled MACl (2.3 g, 22.5 mmol) in 10 ml of dichloromethane was added dropwise. A small amount of inhibitor, tertiary octyl pyrocatechine, was added to prevent polymerization of the monomer. Simultaneously but with a slight delay, 5.6 ml (22.5 mmol) of 4N NaOH was added dropwise to the reaction mixture. After addition of MACl and NaOH the reaction mixture was warmed up to room temperature and allowed to react for one hour. The pH was maintained at around 8-9. The dichloromethane layer was separated from the water layer, washed with 2 ml of water and discarded. The combined aqueous layer was mixed with 40 ml of ethyl acetate. Under vigorous stirring and cooling, dilute HCl was added slowly until the pH reached at 2-3. The organic layer was separated and the aqueous layer was extracted three times with ethyl acetate. The combined organic layer was dried over anhydrous sodium sulfate overnight. The dried solution was filtered and washed with ethyl acetate. The ethyl acetate was removed by rotary evaporation to obtain the product as a white powder. Recrystallization was done from ethyl acetate (melting point: 141.8-143.4° C.). $^1$H NMR (400 MHz, CDCl$_3$): δ 1.96 (s, 3H)), 3.06-3.20 (2m, 2H), 3.85-4.11 (2m, 2H), 4.83-4.85 (m, 1H), 5.41 (s, 1H), 5.79 (s, 1H), 7.20-7.30 (m, 5H).

3) Synthesis of LG-OMe HCl

Leucylglycine-OMe (LG-OMe) was made from the reaction of leucylglycine (LG) and thionyl chloride/methanol as outlined in Scheme 2.

Leucylglycine (Leu-Gly, 4.0 g 21 mmol) was dissolved in 35 ml of methanol and cooled to −15° C. A slight of excess of thionyl chloride (SOCl$_2$) (2 ml, 26 mmol) was added dropwise under stifling. After equilibrating to room temperature the mixture was refluxed for three hours. The solvent was evaporated to dryness and the residue was dissolved in methanol and evaporated again to remove traces of HCl and SOCl$_2$. The residue was dissolved in benzene and evaporated to obtain a white amorphous solid. The crude product (LG-OMe.HCl) was used in subsequent steps without purification. $^1$H NMR (400 MHz, DMSO-d$_6$): δ 0.89-0.93 (m, 6H), 1.56-1.61 (m, 2H)), 1.71-1.78 (m, 1H), 3.65 (s, 3H), 3.77-3.85 (m, 2H), 3.88-4.00 (m, 1H), 5.41 (s, 1H), 5.79 (s, 1H), 7.25-7.28 (m, 5H).

4) Synthesis of MA-GFLG-OMe (SEQ ID NO: 1)

Methacryloylglycylphenylalanylleucylglycine OMe (MA-GFLG-OMe) (SEQ ID NO: 1) was made from the reaction of methacryloylglycylphenylalanine (MA-GF-OH) and leucylglycine-OMe (LG-OMe) as outlined in Scheme 2.

To a solution of 5.0 g of Leu-Gly-OMe HCl (21 mmol) in 40 ml of dimethylformamide (DMF), was added 4.0 g of 1-hydroxybenzonitrile (HOBT, 25 mmol), 4.0 ml of N,N'-diisopropylethylamine (DIEA, 25 mmol) and 6.0 g of MA-Gly-Phe (20.7 mmol). The reaction mixture was stirred and cooled to −10° C. 5.2 g of N,N'-dicyclohexylcarbodiimide (DCC, 25 mmol) in 20 ml of DMF was added dropwise within five minutes. The solution was stirred for two hours at 0° C. and then for 24 hours at room temperature. After overnight stirring the precipitated byproduct, dicyclohexyl urea (DCU) was filtered off. The filtrate was roto-evaporated to remove the DMF completely. The residue was mixed with 40 ml of 5% NaHCO$_3$ solution and extracted with ethyl acetate three times. The extract was washed with 40 ml of 5% citric acid solution, 40 ml of 5% NaHCO$_3$ solution and saturated brine and dried over anhydrous sodium sulfate. After filtering off the drying agent and the filtrate was concentrated under vacuum to obtain the product (MA- GFLG-OMe (SEQ ID NO: 1)). Recrystallization was done from ethyl acetate (melting point: 140.9-143.0° C.).

5) Synthesis of MA-GFLG-OH (SEQ ID NO: 1)

Methacryloylglycylphenylalanylleucylglycine (MA-GFLG-OH (SEQ ID NO: 1)) was made from the hydrolysis of methacryloylglycylphenylalanylleucylglycine OMe (MA-GFLG-OMe (SEQ ID NO: 1)) as outlined in Scheme 2.

To a cooled solution of 6.9 g of MA-GFLG-OMe (SEQ ID NO: 1) (14.5 mmol) in 80 ml of methanol, excess of 1 N NaOH (18 ml, 18 mmol) was added dropwise under stirring. After addition of a small amount of inhibitor (t-octyl pyrocatechine) the reaction mixture was stirred for one and a half hours at 0° C. and then for two hours at room temperature. Additional amounts of DCU byproduct from the previous reaction was precipitated and filtered. The filtrate was concentrated under vacuum to remove methanol, mixed with 160 ml of distilled water and acidified with concentrated citric acid to pH 2.0. The free acid was extracted with 4×200 ml of ethyl acetate, washed with saturated brine and dried over anhydrous sodium sulfate overnight. After evaporation of the solvent under vacuum the tetrapeptide product (MA-GFLG-OH (SEQ ID NO: 1)) was recrystallized from ethyl acetate (melting point: 161.4-165.6° C.). MS (ESI) m/z 483 (M+Na).

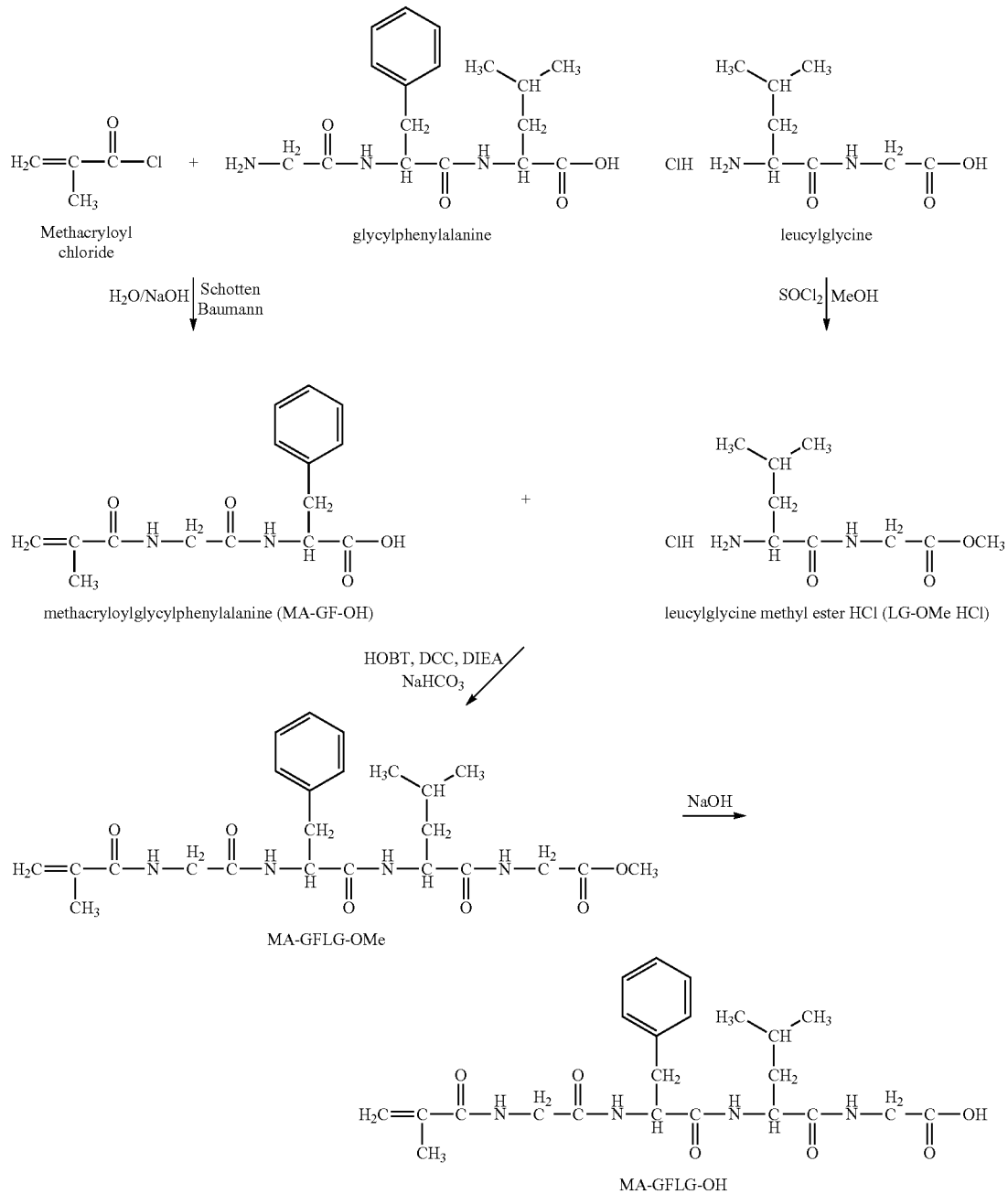

Scheme 2 'GFLG' is disclosed as SEQ ID NO: 1

6) Synthesis of methacryloylglycylphenylalanylleucylglycyl-Gemcitabine (MA-GFLG-Gemcitabine) (SEQ ID NO: 1) (Scheme 3).

To a solution of MA-GFLG-OH (SEQ ID NO: 1) in DMF (1×), a solution of 1-hydroxybenzotriazole (1.2×) was added with constant stirring. The temperature was cooled to −10° C. and a solution of DCC (1.2×) in DMF was added dropwise with stirring. Gemcitabine hydrochloride solution in DMF and N,N'-diisopropyl ethylamine was then added to the reaction mixture dropwise. The reaction mixture was allowed to reach room temperature. The precipitated DCU was filtered off and DMF removed by rotary evaporation. The product was purified by column chromatography (silica gel, eluent: EtOAc/MeOH) and analyzed by mass spectrometry (M+1=706.3) and TLC.

7) Synthesis of methacryloylglycylphenylalanylleucylglycyl-Docetaxel (MA-GFLG-Docetaxel (SEQ ID NO: 1)) (Scheme 4).

MA-GFLG-OH (SEQ ID NO: 1) was dissolved in anhydrous DMF, and to this solution at ° C. were added diisopropylcarbodiimide (DIPC, 1×), docetaxel (1×), and 4-di(methylamino)pyridine (DMAP, 1.5×). The resulting solution was allowed to warm to room temperature and left for 16 h. The reaction mixture was washed with 0.1 N HCl, dried, and evaporated in vacuo to yield the product as a white solid which was purified by column chromatography (silica gel, eluent: EtOAc/MeOH). The product was verified by thin layer chromatography and mass spectroscopy m/z 1272.3 (M+Na).

Scheme 3 'GFLG' is disclosed as SEQ ID NO: 1

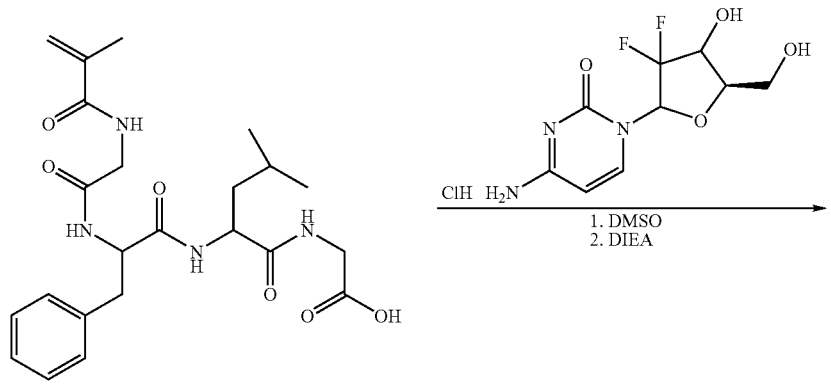

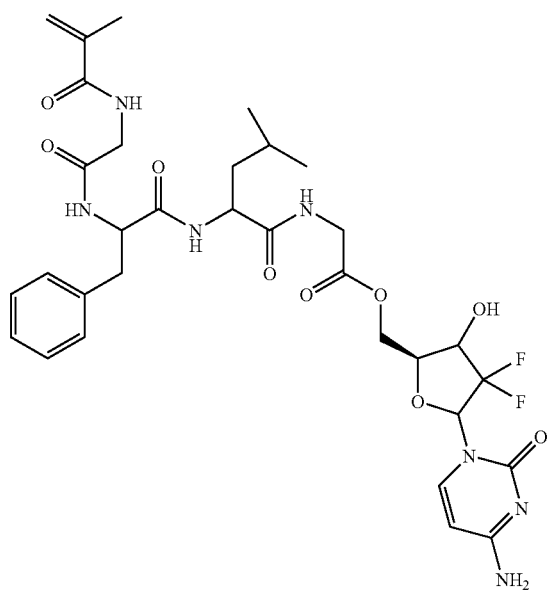

MA-GFLG-Gencitabine

Scheme 4 'GFLG' is disclosed as SEQ ID NO: 1

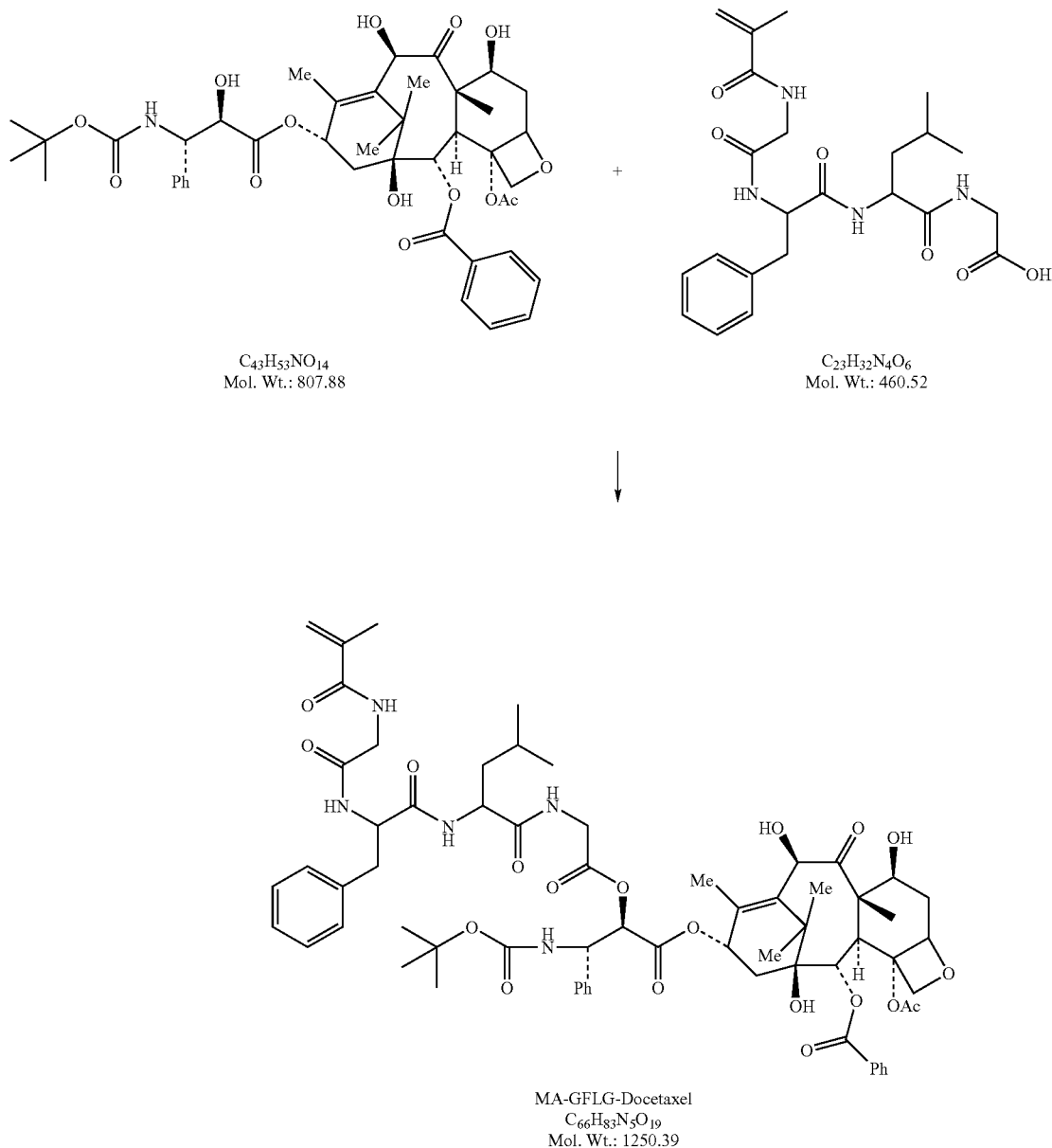

MA-GFLG-Docetaxel
$C_{66}H_{83}N_5O_{19}$
Mol. Wt.: 1250.39

8) Synthesis of Polymer-Drug Conjugates

HPMA copolymer-Drug (wherein Drug represents Gemcitabine and Docetaxel) conjugates were synthesized from the comonomers, by free radical precipitation copolymerization of the comonomers HPMA (86.7 mg, 0.603 mmol) and MA-GFLG-Drug (SEQ ID NO: 1) (5 mg, 0.004 mmol, in case where drug is docetaxol) in acetone (0.72 ml)/DMSO (0.08 ml) at 50° C. for 24 h using N,N'-azobisisobutyronitrile (AIBN, 4.4 mg) as the initiator as shown in Scheme 5. The feed composition of the comonomers was varied to contain 0, 2, and 10 mole % of MA-GFLG-Drug (SEQ ID NO: 1) respectively. The ratio of comonomers:initiator:solvent was kept constant at 12.5:0.6:86.9 wt %. Typically AIBN and HPMA were dissolved in acetone and mixed with a solution of MA-GFLG-Drug (SEQ ID NO: 1) in small amounts of DMSO. The mixture was sealed under nitrogen in an ampoule and left to polymerize with stirring at 50° C. for 24 h. The precipitated polymer was dissolved in methanol and reprecipitated in 20× volume of ether. Small molecular weight unreacted monomers and other impurities were separated from the polymeric conjugates by redissolving in distilled water and dialyzed against distilled water to remove the salts and subsequently lyophilized to obtain the pure product.

Scheme 5 'GFLG' is disclosed as SEQ ID NO: 1.

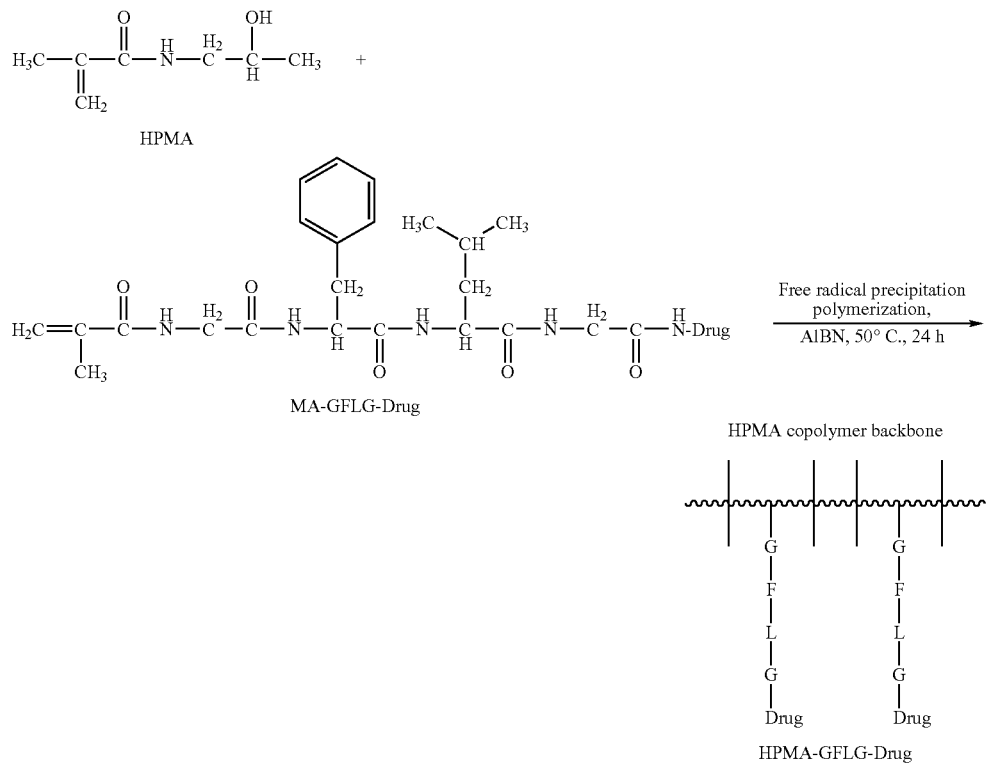

9) Synthesis of HPMA Copolymer-RGDfK-Docetaxel Conjugate.

Polymeric conjugates were synthesized in a two step procedure as outlined in Scheme 6. In the first step the reactive HPMA copolymer-drug conjugates were synthesized by free radical precipitation copolymerization of HPMA, MA-GFLG-Docetaxel (SEQ ID NO: 1) and methacryloylglycylglycine-p-nitrophenyl ester (MA-GG-ONp) comonomers in acetone/5% DMSO. The feed compositions of the comonomers were 89.34%, 0.66% and 10% respectively. N,N'-azobisisobutyronitrile (AIBN) was used as the initiator. Briefly HPMA (54.24 mg, 0.38 mmol), MA-GFLG-Docetaxel (SEQ ID NO: 1) (3.5 mg, 0.0028 mmol) and MA-GG-ONp (13.62 mg, 0.0424 mmol) and AIBN (3.43 mg) were dissolved in 1 ml of acetone (5% DMSO). The ratio of comonomers:initiator:solvent was kept constant at 12.5:0.6:86.9 wt %. The mixture was sealed under nitrogen in an ampoule and left to polymerize with stirring at 50° C. for 24 h. The precipitated polymer precursor was dissolved in methanol and reprecipitated in 20× volume of ether. Small molecular weight unreacted monomers and other impurities were separated from the polymeric conjugates by redissolving in distilled water and dialyzed against distilled water to remove the salts and subsequently lyophilized to obtain the pure product. The ONp content of the polymer was determined spectrophotometrically at 272 nm.

In the second step the targeting peptide RGDfK was conjugated to polymer precursors by an aminolysis reaction. Briefly 35.69 mg HPMA-(GFLG-Docetaxel)-GG-ONp (SEQ ID NO: 1) precursor (containing 0.02 mmol ONp groups) was dissolved in 1.6 ml dry DMF (dried over 3 Å molecular sieves). RGDfK (16.7 mg, 0.03 mmol) was added at 1.3 molar excess to that of the MA-GG-ONp content in the polymeric precursor. The reaction was carried out under nitrogen for 24 h at room temperature. The reaction was terminated with 1-amino-2-propanol (0.02 mmol). The conjugate was dialyzed against deionized water and lyophilized.

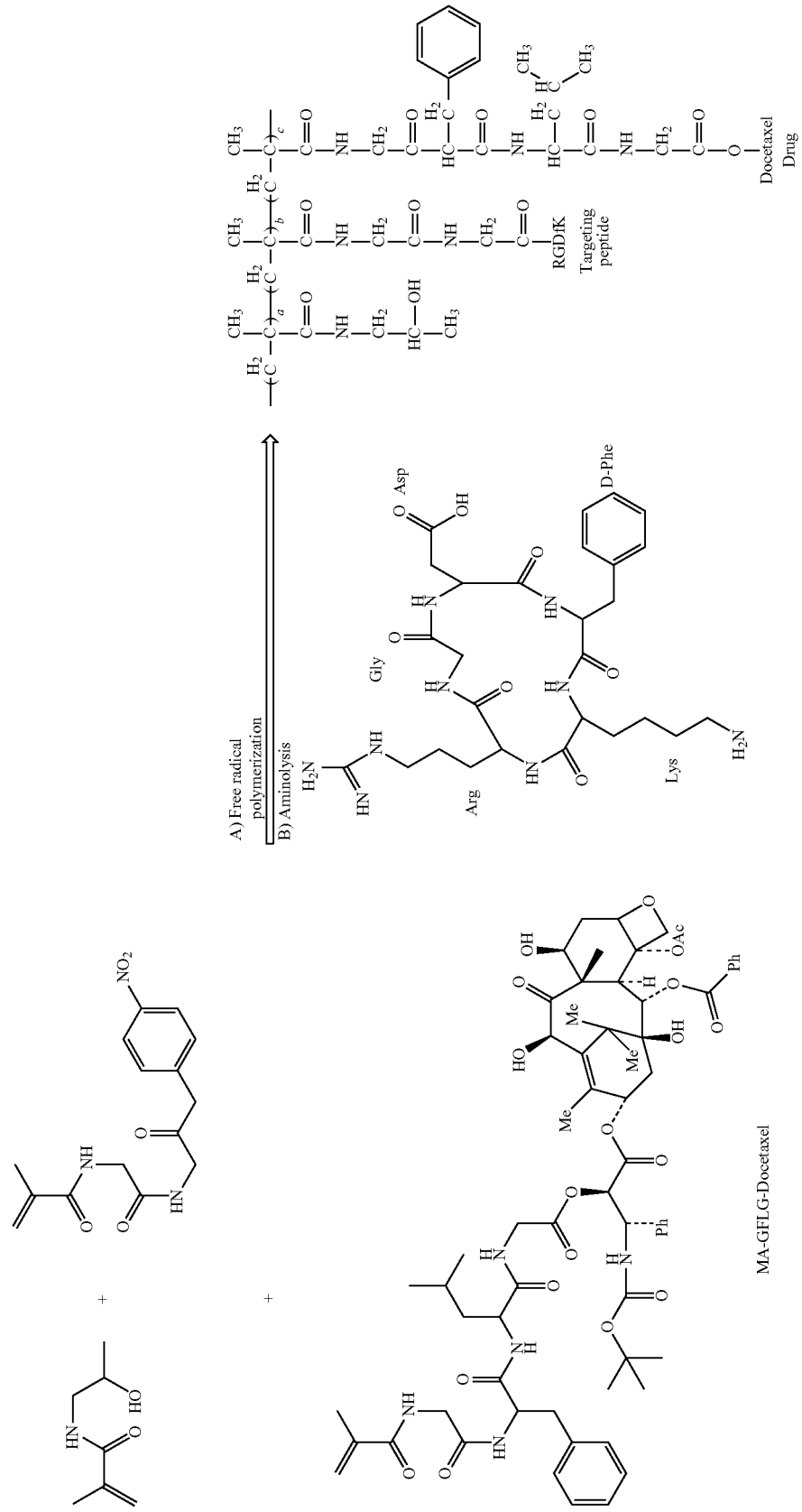
Scheme 6 'GFLG' is disclosed as SEQ ID NO: 1.

10) Synthesis and Characterization of HPMA Copolymer-RGDfK-Gemcitabine Conjugate.

The titled polymer-drug conjugates can be prepared using the similar method to HPMA copolymer-RGDfK-Docetaxel conjugate.

11) Synthesis of HPMA Copolymer-EPPT1-Docetaxel Conjugate or HPMA Copolymer-EPPT1-Gemcitabine Conjugate.

The titled polymer-drug conjugates can be prepared using the similar method to HPMA copolymer-RGDfK-Docetaxel conjugate.

12) Synthesis of HPMA Copolymer-Folate-Docetaxel Conjugate or HPMA Copolymer-Folate-Gemcitabine Conjugate The titled polymer-drug conjugates were prepared using the similar method to HPMA copolymer-RGDfK-Docetaxel conjugate.

13) Physicochemical Characterization of Polymer-Drug Conjugates

A series of polymer drug conjugates were synthesized successfully as listed in Table 1.

The weight average molecular weight (Mw) and polydispersity of the synthesized polymer-drug conjugates were estimated by size-exclusion chromatography using a Superose 12 HR 10/30 column (Amersham Biosciences) on a Fast Protein Liquid Chromatography (FPLC) system (Amersham Biosciences). Samples at 1 mg/ml were eluted at a flow rate of 0.4 ml/min using PBS as the elution solvent. The number average molecular weight (Mn), weight average molecular weight (Mw) and polydispersity (n=Mw/Mn)) of the polymers were estimated from a calibration curve using polyHPMA fractions of known molecular weights. The drug content was obtained using Amino Acid Analysis (Commonwealth Biotechnologies Inc, Richmond, Va.). The results are presented in Table 1. The overall size distributions of the polymers were in agreement with established values reported in the literature on similar systems.

Human MDA-MB-231 (breast), HCT116 (colon) and PANC-1 (pancreas), from the American Type Culture Collection (ATCC) (Manassas, Va.). UMRC2 (kidney) from United States National Cancer Institute (Bethesda, Md.). Cells were maintained in Dulbecco's modified Eagle's medium ("DMEM", Invitrogen) supplemented with 10% FBS, P/S and 10 mM HEPES. All cells were incubated at 37° C. under humidified 5% $CO_2$.

2) In Vitro Cell Proliferation Assay Against Human Tumor Cell Lines

The growth inhibition assay of HPMA-drug conjugates against human cancer cell lines was performed using the Sulforhodamine B ("SRB") method (Skehan et al., J. National Cancer Institute, 82: 1107-1112 (1990)). Briefly, exponentially growing cancer cells were seeded into a 96-well plate at a density of $2-3\times10^3$ cells/well and treated with HPMA copolymer-drug conjugates the next day. Triplicate wells were used for each treatment. Water was used as a control. The cells were incubated with HPMA copolymer-drug conjugates for 96 hours at 37° C. in a humidified 5% $CO_2$ atmosphere. After 96-hour incubation, cells were fixed with 10% trichloroacetic acid ("TCA"), incubated for 1 hour at 4° C., and washed 3 times with tap water. Subsequently, cells were stained with 0.4% sulforhodamine B in 1% acetic acid for 30 minutes, washed 3 times with 1% acetic acid, and air-dried again. After 5 minutes agitation in 10 mM Tris solution, the absorbance of each well was measured at 530 nm using Benchmark Plus Microplate reader (Bio-Rad Laboratories, Hercules, Calif.). The absorbance value provides a direct measure of the number of live cells post-treatment with HPMA copolymer-drug conjugates.

To translate the $OD_{530}$ values into the number of live cells in each well, the $OD_{530}$ values were compared to those on standard $OD_{530}$-versus-cell number curves generated for each cell line. The percent survival was calculated using the formula:

TABLE 1

Physicochemical characteristics of polymer-drug conjugates, 'GFLG' is disclosed as SEQ ID NO: 1.

| | Feed Monomer Composition (mole %) | | | Polymer Characteristics | | |
| --- | --- | --- | --- | --- | --- | --- |
| | | | | Drug Content | | |
| Sample | HPMA | MA-GFLG-Drug | targeting ligand | (mmole/g polymer) | Mw (g/mole) | Mw/Mn |
| HPMA-GFLG-Gemcitabine | 90 | 10 | 0 | 0.4553 | 138 kD | 1.67 |
| HPMA-GFLG-Docetaxel | 95 | 1.25 | 0 | 0.0312 | 167 kD | 1.40 |
| HPMA-GFLG-Docetaxel | 97.5 | 0.66 | 0 | 0.0146 | 133 kD | 1.69 |
| HPMA-GFLG-Gemcitabine-folate | 89.9 | 10 | 0.1 | 0.5 | | |
| HPMA-GFLG-Docetaxel-folate | 98.7 | 1.25 | 0.1 | 0.06 | | |
| HPMA-GFLG-Docetaxel-RGDfK | 89.34 | 0.66 | 10 | 0.04 | 133 kD | 1.69 |

Example 2

Biological Tests

1) Growth of Cancer Cell Lines

Cancer cell lines to determine the effect of HPMA-drug conjugates were obtained from the following sources:

% Survival=live cell number[test]/live cell number [control]×100

The $IC_{50}$ values were calculated by non-linear regression analysis.

Table 2 summarizes the inhibition of cell growth ($IC_{50}$, μM) determined for HPMA copolymer-drug conjugates.

TABLE 2

In-vitro cytotoxicity of free drugs, HPMA-GFLG, HPMA-GFLG-drug conjugates, and HPMA-GFLG-drug-a targeting ligand conjugates against human cancer cell lines.. 'GFLG' is disclosed as SEQ ID NO: 1.

| Drugs | IC$_{50}$ (μM) of drug equivalent | | | |
|---|---|---|---|---|
| | UMRC2 | MDA-MB-231 | PANC-1 | HCT116 |
| Docetaxel | 0.026 | 0.00077 | 0.0012 | 0.00055 |
| Gemcitabine | 0.29 | 0.22 | 0.59 | 0.056 |
| HPMA-GFLG-Docetaxel | 0.033 | 0.0014 | 0.0066 | 0.00099 |
| HPMA-GFLG-Gemcitabine | 5.17 | 2.49 | 5.18 | 1.61 |
| HPMA-GFLG-Docetaxel-folate | 0.068 | 0.0040 | 0.0043 | 0.0028 |
| HPMA-GFLG-Gemcitabine-folate | — | 2.53 | 3.48 | 2.44 |

Example 3

Xenograft Study

In order to observe the inhibition of growth of tumor in an animal model, a nude mouse xenograft model was conducted utilizing HPMA conjugated docetaxel or gemcitabine as described below.

Figure 2:
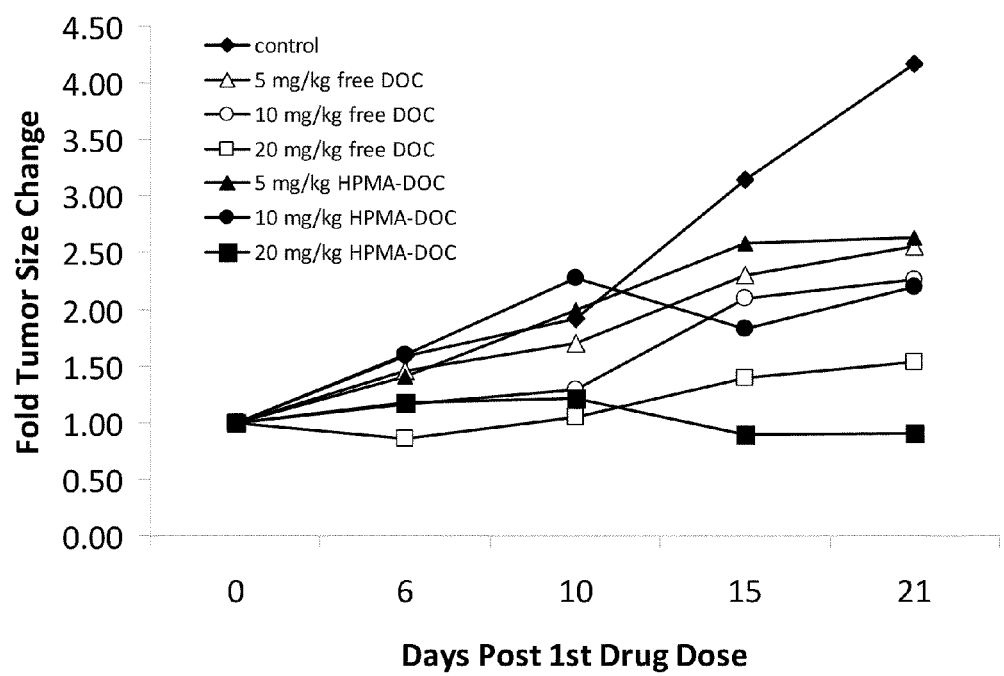
FIG. 2 is a graph showing the inhibition of tumor growth by HPMA-GFLG-docetaxel (DOC) conjugates in nude mice subcutaneously injected with HCT116 human colon carcinoma cells. The efficacy is expressed as fold change in tumor size as a function of time (days).
Figure 3:
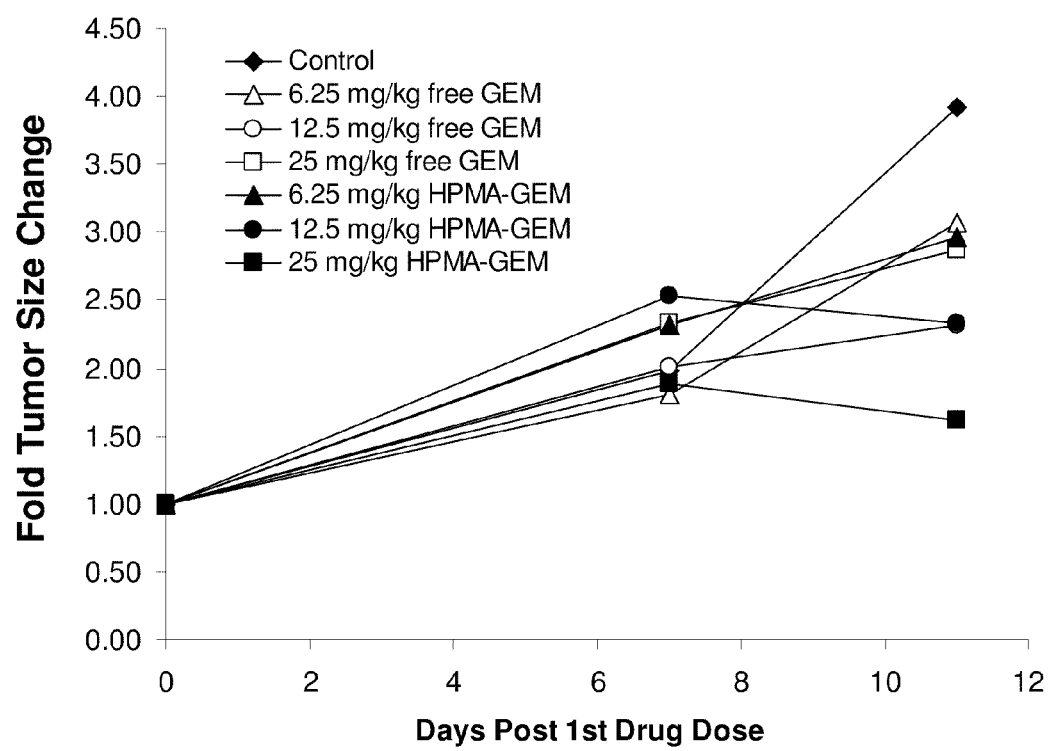
FIG. 3 is a graph showing the inhibition of tumor growth by HPMA-GFLG-gemcitabine (GEM) conjugates in nude mice subcutaneously injected with HCT116 human colon carcinoma cells. The efficacy is expressed as fold change in tumor size as a function of time (days). 'GFLG' is disclosed as SEQ ID NO: 1.

Mia-Paca human pancreatic carcinoma cells or HCT116 cell suspension (3×10$^6$ cells) were injected subcutaneously into the lower flank of six-week-old female FoxN1 null mice on day 0. When tumors reach an appropriate size, for example, a volume of about 50-60 mm$^3$, the mice were injected intravenously every 4-5 days with phosphate buffered saline (PBS) only or with a drug conjugate of the invention. Animals are monitored over several weeks until control tumors reach, for example, a diameter of about 1 cm, when animals are to be euthanized. Tumor size and tumor constituents were determined and reported as a fold of tumor size change (FIG. 1-FIG. 3).

Using the model described in this example it is shown that a drug conjugate of the invention, for example, a drug conjugate described in Example 1, is able to inhibit or stabilize cellular proliferation in vivo supporting its anticancer effects and properties.

What is claimed is:

1. A compound comprising:
   a carrier molecule,
   a linker molecule covalently attached to the carrier molecule,
   a targeting ligand covalently attached to the carrier molecule, optionally through a second linker, and
   an anticancer agent covalently attached to the linker molecule, wherein the anticancer agent is docetaxel, and wherein the carrier molecule comprises poly(N-2-hydroxypropylmethacrylamide) (poly-HPMA).

2. The compound of claim 1, wherein the linker is selected from the group consisting of an amino acid and an oligopeptide.

3. The compound of claim 2, wherein the amino acid or the oligopeptide is selected from the group consisting of Gly-Phe-Leu-Gly (SEQ ID NO: 1), Gly-Ile-Phe, Gly-Val-Phe, Gly-Gly-Phe, Gly-Gly-Phe-Phe (SEQ ID NO: 2), Gly-Ile-Tyr, Phe, Gly, Gly-Gly, Ala, Ser, Gly-Phe, Gly-Leu-Phe, Gly-Phe-Phe, Gly-D-Phe-Phe, Ala-Gly-Val-Phe (SEQ ID NO: 3), Gly-Gly-Val-Phe (SEQ ID NO: 4), Gly-Phe-Tyr, Gly-B-Ala-Tyr, Gly-Leu, Gly-Phe-Gly, His-Ser-Ser-Lys-Leu-Gln (SEQ ID NO: 5) and glutaryl-4-hydroxyprolyl-Ala-Ser-cyclohexaglycyl-Gln-Ser-Leu (SEQ ID NO: 6).

4. The compound of claim 1, wherein the carrier molecule comprises poly-HPMA, and the anticancer agent is linked to the carrier molecule through a GFLG (SEQ ID NO: 1) oligopeptide chain.

5. The compound claim 1, wherein the carrier molecule has a molecular weight of from about 10,000 daltons to about 250,000 daltons.

6. The compound of claim 5, wherein the carrier molecule has a molecular weight of from about 100,000 daltons to about 170,000 daltons.

7. The compound of claim 1, wherein the targeting ligand is selected from the group consisting of RGDfK, EPPT1, and folate.

8. The compound of claim 1, wherein the targeting ligand is covalently attached to the carrier molecule through the second linker, and the second linker comprises an oligopeptide Gly-Gly (GG).

9. The compound of claim 1, wherein the compound circulates in the bloodstream.

10. The compound of claim 1, wherein the targeting ligand is folate.

11. A method of treating cancer comprising administering a therapeutically effective amount of a compound according to claim 1 to a person in need thereof, wherein the cancer is selected from the group consisting of breast cancer, adenocarcinoma, non-small cell lung cancer, prostate cancer, pancreatic cancer, colon cancer, squamous cell carcinoma of head and neck, T-cell lymphoma, small cell lung cancer, gastric cancer, ovarian cancer, melanoma, and esophageal carcinoma.

12. A compound comprising:
    a carrier molecule,
    an anticancer agent covalently attached to the carrier molecule, optionally through a linker molecule, and
    a targeting ligand covalently attached to the carrier molecule, optionally through a second linker molecule, wherein the targeting ligand is selected from the group consisting of RGDfK, EPPT1, and folate, wherein the anticancer agent is docetaxel, and wherein the carrier molecule comprises poly(N-2-hydroxypropylmethacrylamide) (poly-HPMA).

13. The compound of claim 12, wherein the linker is selected from the group consisting of an amino acid and an oligopeptide.

14. The compound of claim 12, wherein the targeting ligand is covalently attached to the carrier molecule through the second linker, and the second linker comprises an Gly-Gly (GG) oligopeptide.

15. The compound of claim 12, wherein the anticancer agent is linked to the carrier molecule through a GFLG (SEQ ID NO: 1) oligopeptide linker, and the second linker is a GG oligopeptide linker.

16. The compound of claim 12, wherein the carrier molecule has a molecular weight of from about 10,000 daltons to about 250,000 daltons.

17. The compound of claim 12, wherein the carrier molecule has a molecular weight of from about 100,000 daltons to 170,000 daltons.

18. The compound of claim 12, wherein the targeting ligand is folate.

19. A method of treating cancer comprising administering a therapeutically effective amount of a compound according to claim 12 to a person in need thereof, wherein the cancer is selected from the group consisting of breast cancer, adenocarcinoma, non-small cell lung cancer, prostate cancer, pancreatic cancer, colon cancer, squamous cell carcinoma of head and neck, T-cell lymphoma, small cell lung cancer, gastric cancer, ovarian cancer, melanoma, and esophageal carcinoma.

* * * * *